United States Patent [19]
Yager et al.

[11] Patent Number: 6,025,139
[45] Date of Patent: *Feb. 15, 2000

[54] METHOD FOR IDENTIFICATION OF MUTATIONS USING LIGATION OF MULTIPLE OLIGONUCLEOTIDE PROBES

[75] Inventors: Thomas D. Yager, Mississauga; James M. Dunn, Scarborough, both of Canada

[73] Assignee: Visible Genetics Inc., Toronto, Canada

[*] Notice: This patent is subject to a terminal disclaimer.

[21] Appl. No.: 09/011,821

[22] PCT Filed: Aug. 28, 1996

[86] PCT No.: PCT/US96/14020

§ 371 Date: Feb. 23, 1998

§ 102(e) Date: Feb. 23, 1998

[87] PCT Pub. No.: WO97/08344

PCT Pub. Date: Mar. 6, 1997

Related U.S. Application Data

[63] Continuation-in-part of application No. 08/590,503, Jan. 24, 1996, Pat. No. 5,888,731.

[60] Provisional application No. 60/003,038, Aug. 30, 1995.

[51] Int. Cl.[7] ............................... C12Q 1/68; C12P 19/34; C07H 21/02; C07H 21/04; C12N 15/00

[52] U.S. Cl. .......................... 435/6; 435/91.2; 536/23.1; 536/24.3; 935/76; 935/77; 935/78

[58] Field of Search ..................... 435/6, 91.2; 536/23.1, 536/24.3; 935/76, 77, 78

[56] References Cited

U.S. PATENT DOCUMENTS

| | | |
|---|---|---|
| 4,719,180 | 1/1988 | Eaton et al. . |
| 5,042,272 | 8/1991 | Hartley ...................................... 435/91 |

(List continued on next page.)

FOREIGN PATENT DOCUMENTS

| | | |
|---|---|---|
| 0185494 | 6/1986 | European Pat. Off. . |
| 320308 | 6/1989 | European Pat. Off. . |
| 439182 | 7/1991 | European Pat. Off. . |
| 477972 | 4/1992 | European Pat. Off. . |

(List continued on next page.)

OTHER PUBLICATIONS

Barany, F., "Genetic disease detection and DNA amplification using cloned thermostable ligase" Proc. Natl. Acad.Sci. USA vol. 88, pp. 189–193 (1991).

Grossman et al., "High–density multiplex detection of nucleic acid sequences oligonucleotide ligation assay and sequence–coded separation"Nucleic Acids Research vol. 22 No. 21 pp. 4527–4534 (1994).

(List continued on next page.)

*Primary Examiner*—W. Gary Jones
*Assistant Examiner*—Ethan Whisenant
*Attorney, Agent, or Firm*—Oppendahl & Larson LLP

[57] ABSTRACT

A ligase-based assay which relies only upon knowledge of the wild-type sequence of a gene or gene fragment is used to detect all types of mutations, i.e., point mutations, insertions and deletions. The assay makes use of a set of oligonucleotide probes, which may be packaged in kit form, which hybridize in series along the length of the gene. The ligation of the probes together form a ligation product, the size of which is evaluated. When the gene or gene fragment being analyzed corresponds to the normal sequence and thus perfectly matches the probes, all of the probes in the set are ligated together, and the ligation produce has a certain resulting size. When a mutation appears in the gene, the hybridization of the probe overlapping the mutation is impaired, with the result that some or all of the ligation produce is of smaller size. By evaluating the size of the ligation product, both the existence of a mutation and its approx. position can be identified.

28 Claims, 10 Drawing Sheets

U.S. PATENT DOCUMENTS

| | | |
|---|---|---|
| 5,132,215 | 7/1992 | Jayaraman . |
| 5,219,734 | 6/1993 | Royer et al. ................................. 435/6 |
| 5,366,877 | 11/1994 | Keith ...................................... 435/91.2 |
| 5,650,274 | 7/1997 | Kambara et al. ........................... 435/6 |
| 5,792,607 | 8/1998 | Backman et al. ........................... 435/6 |
| 5,800,994 | 9/1998 | Martinelli et al. .......................... 435/6 |
| 5,866,337 | 2/1999 | Schon ......................................... 435/6 |
| 5,888,731 | 3/1999 | Yager et al. ................................ 435/6 |

FOREIGN PATENT DOCUMENTS

| | | |
|---|---|---|
| 9115600 | 10/1991 | WIPO . |
| 93/00447 | 1/1993 | WIPO . |
| 93/20227 | 10/1993 | WIPO . |
| 93/20240 | 10/1993 | WIPO . |
| 94/03636 | 2/1994 | WIPO . |
| 94/08047 | 4/1994 | WIPO . |
| 94/16105 | 7/1994 | WIPO . |
| 94/24143 | 10/1994 | WIPO . |
| 94/24311 | 10/1994 | WIPO . |
| 95/11996 | 5/1995 | WIPO . |
| 9527078 | 10/1995 | WIPO . |

OTHER PUBLICATIONS

Landegren et al., "A Ligase–Mediated Gene Detection Technique" Science vol. 241 pp.1077–1080 (1988).

Marsh et al., "Pyrococcus furious DNA Ligase and the Ligase Chain Reaction" Strategies in molecular biology vol. 5 pp. 73–76.

Rouwendal et al., "Simultaneous Mutagenesis of Multiple Sites: Application of the Ligase Chain Reaction Using PCR Products Instead of Oligonucleotides" Circle Reader Service No. 172 vol. 15 pp. 68–75 (1993).

Wu et al., "Specificity of the nick–closing activity of bacteriophage T4 DNA ligase" Gene 76 pp. 245–254 (1989).

Weisberg et al., "Simultaneous Mutagenesis of Multiple Sites: Appication of the Ligase Chain Reaction Using PCR Products Instead of Oligonucleotide", *Biotechnique*15: 68–76 (1993).

Nickerson et al., "Automated DNA Diagnostics Using an ELISA–based Oligonucleotide Ligation Assay", *Proc. Nat'l Acad. Sci.* (USA) 87: 8923–8927 (1990).

METHOD FOR IDENTIFICATION OF MUTATIONS USING LIGATION OF MULTIPLE OLIGONUCLEOTIDE PROBES

This application is a 371 of WO 9,527,078 filed Apr. 3, 1995 and a continuation-in-part of U.S. patent application Ser. No. 08/590,503, filed Jan. 24, 1996, now U.S. Pat. No. 5,888,731, which claims priority from U.S. Provisional Application Ser. No. 60/003,038 filed Aug. 30, 1995.

BACKGROUND TO THE INVENTION

This application relates to a method for the detection of mutations, including previously unknown mutations, in a gene or a gene fragment having a known wild-type sequence.

Many diseases and conditions have been found to be associated with genetic mutations, and more such associations are being identified as time goes by. In some cases, such as sickle-cell anemia, a single base change has been identified as the causative mutation. More generally, however, many different mutations may manifest themselves as a single disease. To test for each of these mutations individually using hybridization-based tests would require the development of as many different probes as there are mutations. Such an effort would involve substantial expense, however, such that in most cases hybridization-based diagnostics are only available for the most prevalent mutations. Furthermore, because development of mutation-specific hybridization-based diagnostics requires knowledge of the mutant sequence, development of diagnostic tests must await the identification and characterization of any given mutation in at least one individual.

The present invention overcomes some of the limitations of hybridization-based diagnostics by providing an assay which relies only upon knowledge of the wild-type sequence, and which detects all types of mutations, i.e., point mutations, insertions and deletions. The method involves the use of a set of oligonucleotide probes which hybridize in series along the length of the gene; the ligation of the probes together to form ligation products; and the evaluation of the sizes and quantities of the ligation products. When the gene being analyzed corresponds to the normal sequence, a characteristic pattern of ligation products is formed, including a substantial amount of full length product which results from all of the probes in the set being ligated together. When a mutation appears in the gene, the hybridization of the probe overlapping the mutation is impaired, with the result that some or all of the ligation product is of smaller size. By evaluating the sizes and quantitites of the ligation products; both the existence of a mutation and its approximate position can be identified. A definitive identification of the mutation can then be made by direct sequencing over a very restricted set of positions.

EP-A-0 185 494 discloses an assay for detection of specific nucleotide sequences in which two oligonucleotide probes which perfectly match adjacent portions of the expected sequence are hybridized and then ligated together. The assay is said to improve reliability over a plain hybridization assay, since it is unlikely that both probes would bind to a spurious location in ligatable proximity.

Ligase enzymes have previously been used in diagnostics for the detection of known point mutations. As described in Landegren et al., "A Ligase-Mediated Gene Detection Technique", *Science* 241: 1077–1080 (1988), and as shown in FIG. 1, this technique involved hybridization of two probes 1 and 1' to the target gene fragment 2 being analyzed. The probes 1 and 1' are selected such that the terminal base in one fragment aligns with the known mutation site when this probe is hybridized with the target gene fragment. The terminal base of the other probe aligns with the base immediately adjacent to the known mutation site. When the probes are completely complementary to the target sequence, T4 DNA ligase will couple the two probes together into a single fragment. When a mutation is present, however, the absence of hybridization at the end of one of the probes will prevent (or at least substantially reduce) the amount of ligation which occurs. By labeling one probe fragment with a capture moiety such as biotin, and the other probe fragment with a radiolabel, Landegren et al. were able to identify the presence or absence of the specific point mutation based upon formation (or non-formation) of the ligated molecule which incorporated both the capture moiety and the radiolabel.

The basic technique described by Landegren et al. has been modified by a number of researchers. For example, F. Barany, "Genetic Disease Detection and DNA Amplification Using Cloned Thermostable Ligase", *Proc. Nat'l Acad. Sci. USA* 88: 189–193 (1991) described the use of a thermostable ligase in place of the T4 DNA ligase utilized by Landegren et al. This enzyme allowed the use of higher temperatures which improved the discrimination between perfectly matched and mismatched sequences. Like the basic Landegren et al. technique, however, Barany only addressed detection of the known point mutations using a pair of probes which meet at the site of the mutation.

A further modification of the Landegren et al. technique is described in PCT Patent Publication No. WO 94/08047 entitled "Ligase Chain Reaction Method for Detection of Small Mutations." In this application, deletion mutations of up to about 5 bases are detected using ligation of a pair of probes. As in the basic Landegren technology, however, a complete knowledge of the site and nature of the mutation is necessary to carry out the test.

It is an object of the present invention to overcome this fundamental limitation of known tests which utilize ligase, and to provide a test methodology which permits the detection of mutations including previously unknown and uncharacterized mutations, whether large or small in magnitude, within a gene of clinical or diagnostic importance.

It is a further object of the present invention to provide kits which may be used in carrying out this method.

SUMMARY OF THE INVENTION

These and other objects of the invention are achieved by a method for detection of mutations within a gene or gene fragment in a sample, said gene or gene fragment having a known wild-type sequence. In accordance with this method, the sample is combined with at least three species of oligonucleotide probes under hybridization conditions. The species of oligonucleotide probes have sequences which are complementary to and hybridize with sequential and contiguous portions of the wild-type sequence, whereby a hybrid is formed between the gene or gene fragment in the sample and at least a first species of oligonucleotide probe. The hybridized oligonucleotide probes are then exposed to ligating conditions. Those oligonucleotide probes which hybridize to the gene fragment in ligatable proximity to one another are ligated together to form one or more species of ligation products. Finally, the lengths and quantities of the species of ligation products are determined. A deviation between the lengths and/or quantities of the ligation products and standard (i.e., wild-type) values for lengths and/or quantities is indicative of the presence and approximate location of a mutation in the gene or gene fragment in the sample.

BRIEF DESCRIPTION OF THE DRAWINGS

FIGS. 15A–5D shows results for analysis of exon 8 of the RB1 gene.

DETAILED DESCRIPTION OF THE INVENTION

Figure 1:
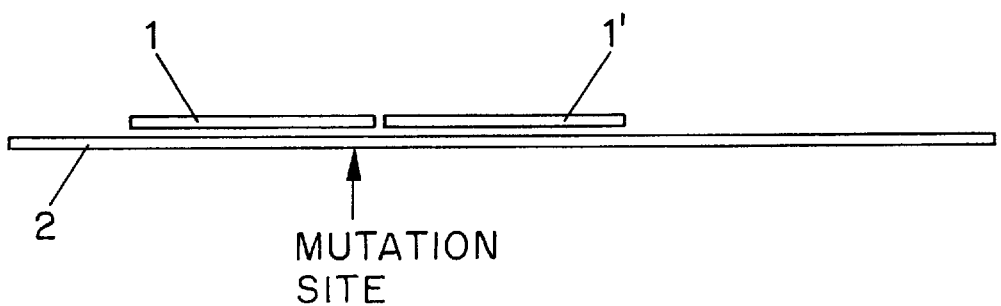
FIG. 1 shows a prior art technique for ligase-mediated detection of point mutations.

The present invention provides a novel method for detecting mutations, including previously unknown and uncharacterized mutations of many different types, in a gene or gene fragment of known wild-type sequence. The method of the invention is of particular utility in detecting mutations within genes or gene fragments the mutation of which is known to be associated with disease conditions, and provides a mechanism for the effective screening of many individuals for possibly disease-related mutations.

As used herein, the term gene or gene fragment may refer to a complete gene, to an individual exon of a gene, or to an arbitrarily selected gene fragment. Such gene or gene fragment may be geneomic DNA, cDNA, RT-PCR amplified fragments, or PCR-amplified genomic fragments. It may be desirable to treat large genes containing multiple exons in several parts, while smaller genes may be evaluated in one step.

The genes or gene fragments which may be analyzed for mutations in accordance with the present invention are those which have a known wild-type sequence at least in the region of diagnostic or clinical significance. For example, the method can be generally employed to determine the presence or absence of mutations in other genes, such as RB1, p53, p16, p21, VHL, HLA genes, CF and all other genes where mutations may sporadically arise. It will be appreciated that some genes are present in several known allelic forms each of which is fairly considered "normal" in that the several forms are not associated with any disease condition. The present invention is fully applicable to these genes by simply performing the analysis using a set of probes for each allelic type and evaluating the results of the tests in concert. Depending on the frequency distribution of the various normal types, these tests may be performed sequentially (e.g., when one type is more prevalent than all others) or concurrently.

Regardless of whether an entire gene or a fragment of a gene is evaluated, the basic steps of the method are the same. One embodiment of this basic methodology is shown diagrammatically in FIG. 2. As shown, in the first step of the method, a set of a plurality of oligonucleotide probes A, B, C, D, and E are hybridized with a target single-stranded gene or gene fragment T. The set of oligonucleotide probes is designed to exactly complement the wild-type target DNA sequence T without nicks, gaps, overlaps, or mismatches. When a mutation is present in the target DNA T, as in the case of the portion aligned with probe D in FIG. 2, the hybridization of probe to the target DNA T is disrupted.

The next step of the method is the ligation of the hybridized oligonucleotide fragments. This ligation is performed at a temperature slightly below the average melting temperature of the probe-wild-type target hybrids. If a mutation exists in the target DNA T, the mismatch between the target DNA T and the oligonucleotide probe D causes the target -oligonucleotide D hybrid to display a lower Tm value than if it were perfectly matched to a wild-type target sequence. As a result, oligonucleotide probe D hybridizes poorly to the target sequence T and is not ligated, or is ligated inefficiently to adjacent oligonucleotide probes C and E.

Figure 2:
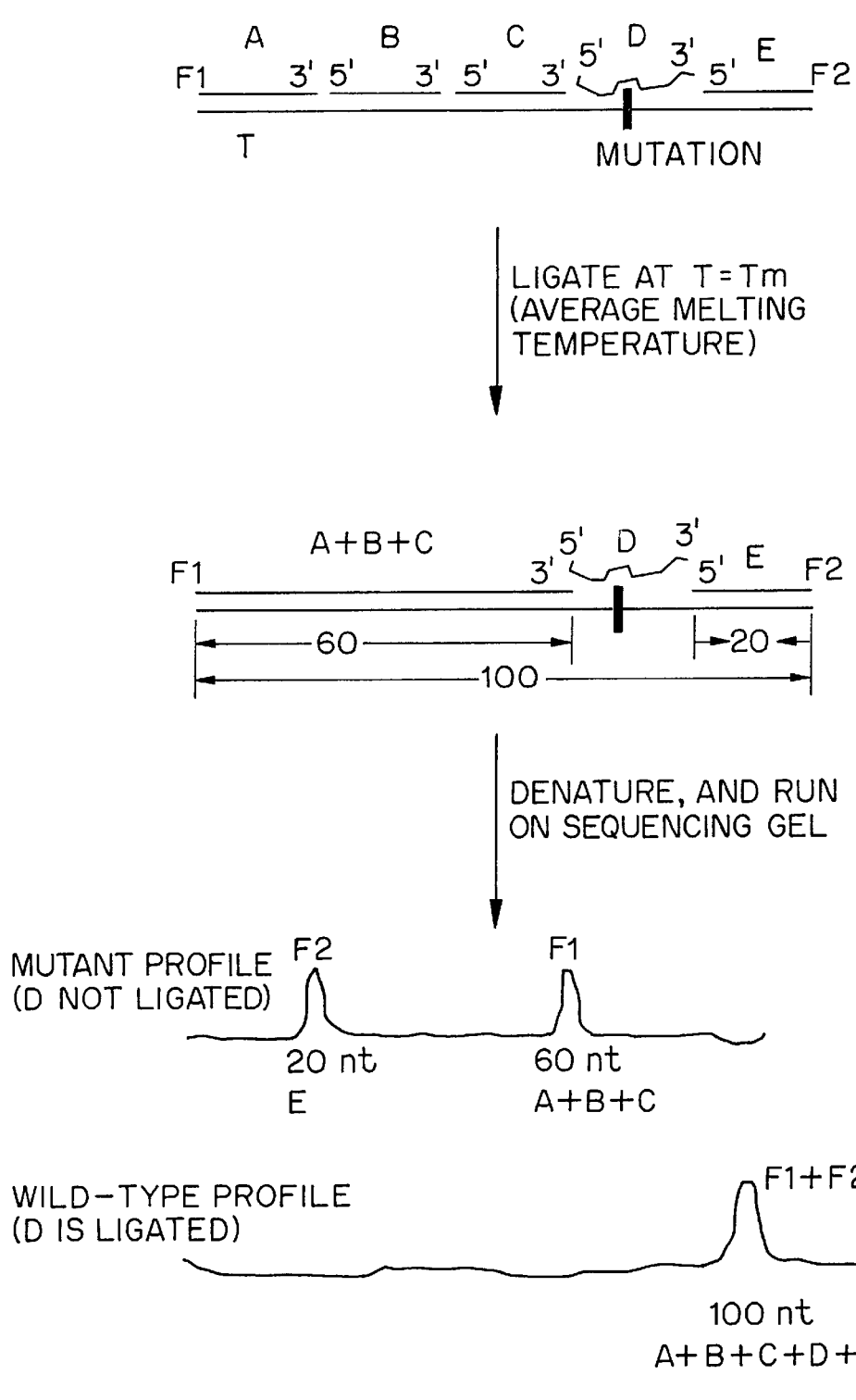
FIG. 2 shows an embodiment of the method of the present invention diagrammatically.

The next step in the method shown in FIG. 2 is denaturation of the ligated strand from the target and detection of the size of the ligated products using fluorescent labels F1 and F2, which can be the same or different, and which were attached to probes A and E, respectively. When the target conforms to the wild-type and is perfectly complementary to the oligonucleotides probes, the product detected is one which has a length corresponding to the sum of probes A+B+C+D+E. In contrast, when a mutation occurs in the segment alignment with probe D two products are detected, one which results from the ligation of probes A+B+C, and one which is merely probe E. Probe D is not detected, because it does not have a fluorescent label.

Figure 3:
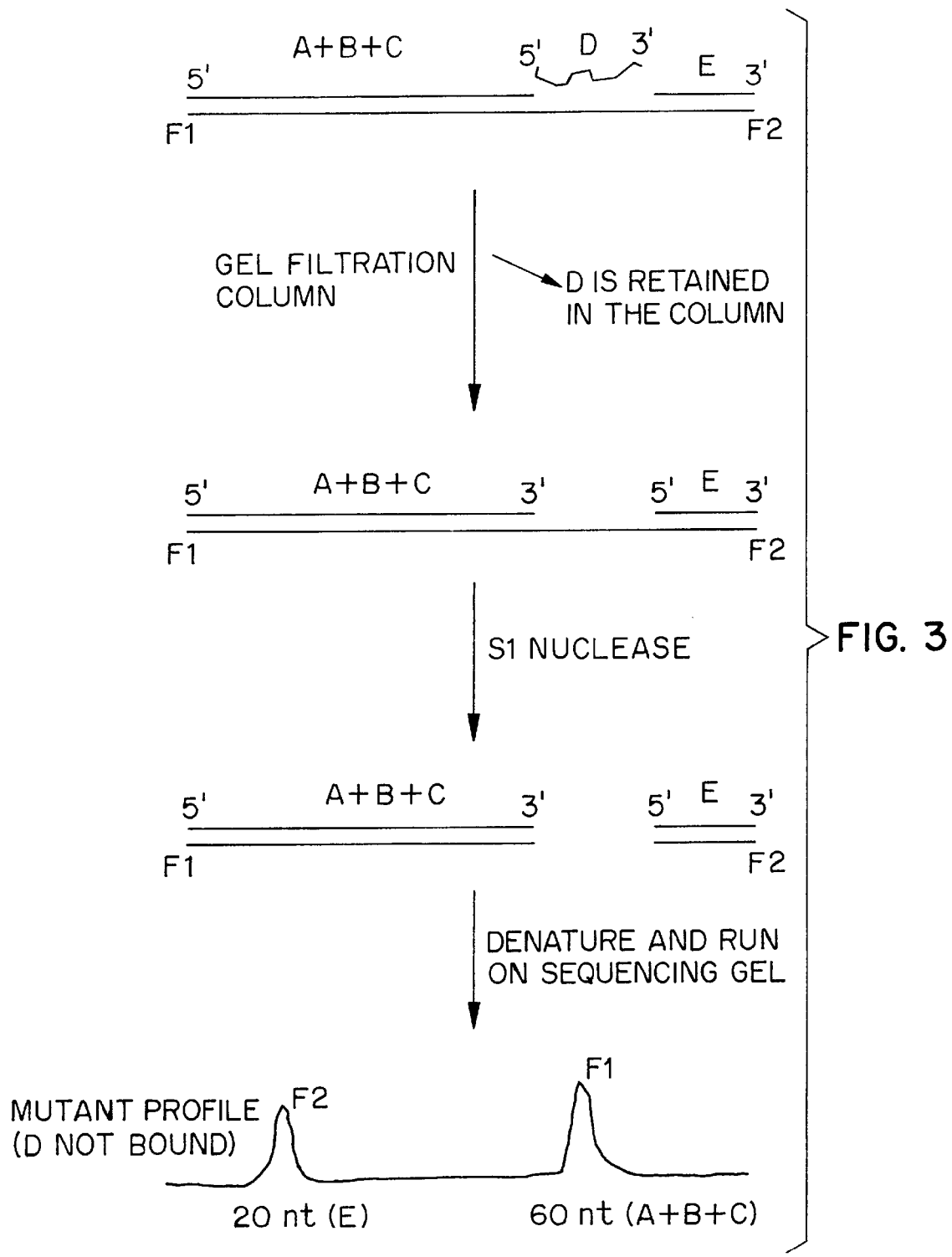
FIG. 3 shows a second embodiment of the method of the present invention diagrammatically.

FIG. 3 shows an alternative embodiment of the method of the invention. In this case, the labels F1 and F2 are attached to the ends of the target DNA sequence rather than to the oligonucleotide probes, for example during a prior amplification reaction using fluorescently-labeled primers or post-amplification end-labeling using conventional chemical or enzymatic methods. After ligation, the ligated hybrid is passed through a gel filtration column to remove the mismatched D probe. S1 Nuclease is then used to digest the single stranded portion the labeled target DNA. The digested hybrids are then denatured, and the single stranded products analyzed for fragment length in the same manner as in FIG. 2.

FIGS. 2 and 3 illustrate the present invention in theoretical terms, assuming perfect discrimination between mutant and non-mutant forms. In practice, this level of discrimination will rarely if ever be achieved, nor is it necessary to the successful practicing of the invention. Analysis of results thus requires a knowledge of the expected ratios of reaction products, which may be obtained by ligation of oligonucleotides against a wild-type template for the system of interest.

In actual practice, what is observed is a mixture of ligation products, including some full-length products, and varying amounts of intermediate ligation products of each possible shorter length. When a mutation is present, the relative amounts of each type of intermediate product shifts, indicating both the fact that there is a mutation, the approximate location of the mutation, and whether the mutation is homozygous or heterozygous. One useful way to evaluate the results of the present test is to obtain a ratio of the height for each intermediate peak to a control peak included in the same sample. When the observed ration falls outside a standard range of values considered "normal," the sample is identified as containing a mutation.

The control peak used to determine the ratios can be any of several different types. First, it can be the peak associated with the full length ligation product. When no mutation is present, the full ligation product is generated in much greater quantities (e.g. 3 to 14 times greater) than any other ligation product. When a mutation is present, the ratio of full-length product to any ligation intermediate falls substantially, i.e., to about 1:1 or below.

Second, as an alternative to the use of the full length as a control, when the sample has been previously amplified by PCR, it is possible to utilize the complementary PCR product as an internal standard by using a labeled primer for formation of this product during the PCR step. The labeled full length PCR product, which is larger than the full length ligation product, can serve both as an internal standard for determining normalized peak heights and as a confirmation of the success of the PCR reaction. The PCR primer used to produce the complementary strand for this purpose can be labeled with the same label affixed to the oligonucleotide probe set, or with a different label. A different label is preferred if an instrument is available to detect two different labels, since this facilitates quantitation of the both a large standard peak and smaller ligation product peaks.

Within the scope of the two basic methodologies shown in FIGS. 2 and 3, it will be appreciated that a great many variations are possible. For example, the target sequence which is analyzed typically will be an exon or gene fragment having a length of about 50 to 200, and preferably about 100 nucleotides in a human gene which has been implicated in some genetic disease. Shorter sequences may be selected for evaluation, particularly where the locus of disease associated mutations is known to be relatively small. Larger target sequences may also be evaluated, although it will be appreciated that information about the presence of multiple mutations could be lost if too large a target sequence was used.

The oligonucleotide probes and the ligation conditions used in the invention are optimized on a gene-by-gene basis to provide the greatest degree of discrimination between normal and mutant forms of the gene. This optimization will of necessity include some empirical observations, but a number of basic principles can be applied to selection of a suitable starting point for final optimization.

The oligonucleotide probes useful in the invention will generally be prepared in sets of from 3 to 10 probes, preferably 5 to 10 probes, with each probe having a length of from about 15 to 25 oligonucleotides. Smaller probes could be used in some cases, but will generally be less desirable because they will lack the specificity for a single site on the target DNA sequence. Longer probes can also be used, but are less desirable for several reasons: (1) very long probes reduce the accuracy with which the location of a detected mutation can be localized; and (2) point mismatches in the middle of very long probes may not significantly affect hybridization to the target, and therefore would remain undetected if long probes were used.

The probes within a set may all be the same size, but more likely will have slight variations in size to equalize the thermodynamic stabilities and equilibrium melting temperatures of the hybrids. These length adjustments are made in a coordinated fashion so that no gaps or overlaps are introduced between adjacent oligonucleotide probes. Thermodynamic parameters of individual probes may be estimated by multiple iterations using a program such as "Oligo" (available from National Biosciences, Inc.) designed to calculate such parameters. (Rylchik et al., "A computer program for choosing optimal oligonucleotides for filter hybridization, sequencing and in vitro amplification of DNA", Nucl Acids Res. 17: 8543–8551 (1989).

In this fashion, the oligonucleotides probes within any given set are designed to have approximately equal Tm values as computed on the basis of perfect match to the wild-type target sequence. The melting temperature Tm for a given probe can be estimated, to a first approximation, using the following equation (Gralla & Crothers, 1973; Borer et al., 1973) which allows melting temperatures to be predicted from a simple two-state (all-or-none) model:

$$Tm = \frac{\Delta H°}{(\Delta S° + R\ln(C/4))} \tag{1}$$

where Tm=equilibrium melting temperature, $\Delta H°$=standard enthalpy of duplex formation, $\Delta S°$=standard entropy of duplex formation, R=universal gas constant, and C=total concentration of single strands (whether melted or hybridized together). This formula is based on the fundamental $\Delta S=\Delta H/T$ relation of equilibrium thermodynamics and assumes a reversible two-state melting transition between complementary strands. In the standard state, each macromolecular species is present at 1M concentration. The R ln (C/4) term in the equation describes the cratic effect of diluting the probe and target away from the 1M standard state.

To apply this equation to estimate the average melting temperature of a set of oligonucleotide probes, it is necessary to have average values of $\Delta H°$ and $\Delta S°$. These can be obtained by viewing an oligonucleotide probe-target hybrid as a plurality of "stacks." A "stack" is a pair of adjacent base-pairs that resides within a longer nucleic acid duplex. A duplex that is N base pairs long will contain N-1 stacks. We assume the average (temperature-independent) values $\Delta H°=-8.34$ kcal/mole and $\Delta S°=-21.04$ cal/K mol for formation of individual "stacks" in a duplex (Breslauer et al., "Predicting DNA duplex stability from the base sequence", Proc. Natl. Acad. Sci. USA 83: 3746–3750 (1986).) To obtain average values of $\Delta H$ and $\Delta S$ for the N-mer, the values for an average "stack" are multiplied by the factor (N-1).

Figure 4:
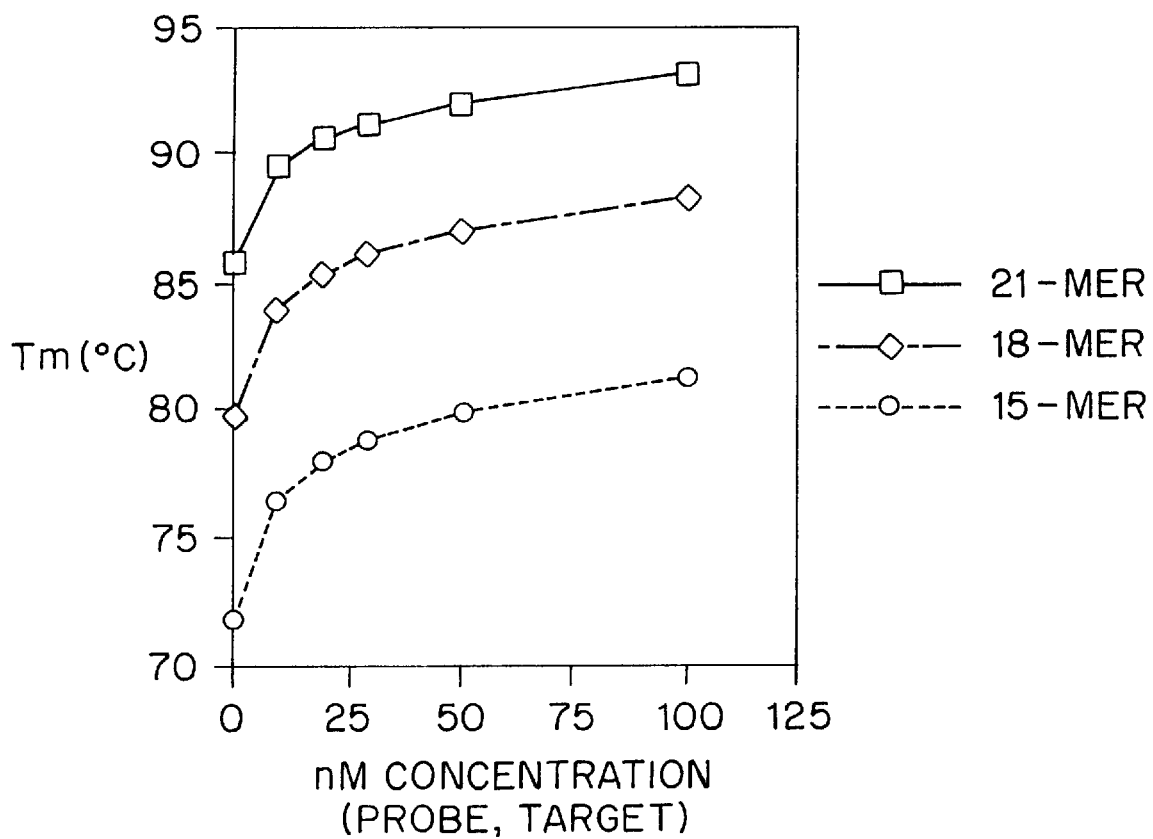
FIG. 4 presents an estimate of Tm as a function of oligonucleotide length and concentration in a typical ligation buffer.

FIG. 4 presents an estimate of Tm as a function of oligonucleotide length and concentration in a typical ligation buffer (1 M NaCl, ~10 mM $Mg^{2+}$). This estimate is computed as an average over all possible sequences, using eq. (1) under the assumption of a perfect match between the oligonucleotide and its target. This figure predicts a Tm value of ~85° C. for an individual 20-mer under typical ligation conditions (10 nM probe and 10 nM target).

The sharpness of the melting transition can also be a significant factor in the method of the present invention. Thus, in addition to selecting oligonucleotide probes having the same melting-temperatures, the probes should also each melt over a narrow temperature range, i.e., of 10 degrees C. or less. If the melting transition is not sharp, then the melting curves for matched and mismatched oligonucleotides will not be clearly separated, and the assay may yield ambiguous results. Fortunately, oligonucleotides as short as 20-mers have sharp melting transitions (Patel et al., "Premelting and melting transitions in the d(CGCGAATTCGCG) self-complementary duplex in solution", Biochemistry 21, 428–436 (1982), Vesnaver et al., "The contribution of DNA single-stranded order to the thermodynamics of duplex formation", Proc. Natl. Acad. Sci. USA 88, 3569–3573 (1991).)

The "sharpness" of a melting transition can also be analyzed at the quantitative level (Gralla et al., "Free energy of imperfect nucleic acid helices, III. Small internal loops resulting from mismatches", J. Mol. Biol. 78: 301–319 (1973).) In a two-state (all-or-none) transition, the temperature-dependence of the equilibrium constant is given by the equation:

$$\frac{\delta \ln K}{\delta(1/T)} = -\frac{\Delta H^\circ}{R}. \quad (2A)$$

For an associating system which consists of equal total concentrations of probe and target, the equilibrium constant can be written in terms of the total probe concentration $[A]_T$ (i.e. free probe+bound probe) and the fraction ($\theta$) of probe that is bound to the target (Gralla et. al.):

$$K = \frac{\theta}{[A]_T(1-\theta)^2} \quad (2B)$$

We substitute eq. (2B) into eq. (2A), and then convert differentials from $\delta/\delta(1/T)$ to $(-T^2)\delta/\delta T$. This leads to the following equation:

$$\frac{\delta \theta}{\delta T} = \left[\frac{\Delta H^\circ}{RT^2}\right]\theta(1-\theta)(1+\theta). \quad (2C)$$

Thus the "sharpness" of a melting curve, as defined by the slope of $\delta\theta/\delta T$ at $T=T_m$, is directly proportional to the absolute magnitude of $\Delta H^\circ$, the standard enthalpy of duplex formation.

Because G:C pairs have a greater absolute magnitude of the enthalpy of formation than do A:T pairs, the transition will be sharper for GC pairs. There are two approaches to equalize the sharpness of the melting transition for different oligonucleotides. First, all oligonucleotides can be made with the same G/C composition. According to eqn. (2C), the (G+C) percentage should be on the high side, to maximize the sharpness of melting. Alternatively, an isostabilizing solvent, such as 5 M betaine, could be used to eliminate the differences in melting temperature between A:T and G:C base pairs (Rees et al., 1993). However, the effect of such solvent on the activity of a thermostable DNA ligase is not known.

Once suitable probes are selected based upon the wild-type sequence of the gene or gene fragment of interest, the probes are hybridized en masse to the target DNA strand. The conditions for this hybridization should meet two main criteria:

(1) they should be compatible with the ligase enzyme selected for use in the ligation step so that ligation of properly hybridized probes can occur; and (2) they should be sufficiently stringent that a significant stability difference exists between perfectly-matched and mismatched hybrids. It will be understood that "compatible" does not mean optimized, and the conditions need only be such that the ligase enzyme functions to produce ligated products within a reasonable period of time. Similarly, the difference between perfectly-match and mismatched hybrids does not have to be absolute, and in fact need only be sufficient to produce a detectable difference in size distribution of the ligation products.

As a general rule, these conditions can be met by performing the ligation somewhat below the average melting temperature Tm of the oligonucleotide probes as predicted by equilibrium thermodynamics. The temperature selected for any given set of probes and ligase represents a compromise between three major competing factors.

First, mismatch ligation is suppressed at high temperatures. The basis for this effect is that a mismatched oligonucleotide has a depressed Tm relative to that of a perfectly matched oligonucleotide, and thus relative to that of other oligonucleotides in the probe set. This first factor favors performing the ligation at a higher temperature.

Competing with this effect, however, is end-fraying. It is known from the literature that significant end-fraying that may interfere with ligation begins to occur as the temperature is raised to within approximately 20° C. of the Tm. (Patel, D. J., Biochemistry 13, 2396 (1974); Putnam et al., "Resonant and localized breathing modes in terminal regions of the DNA double helix", Biophys. J. 35: 271–287 (1981); Zuiderweg et al., "1H NMR studies of lac-operator DNA fragments", Nucl. Acids Res. 9: 6553–6569 (1981); Patel et al., supra, (1982); Schmitz et al., "Solution structure of a DNA octamer containing the Pribnow box via restrained molecular dynamics simulation with distance and torsion angle constraints derived from two-dimensional nuclear magnetic resonance spectral fitting", J Mol Biol 227: 510–31 (1992).) Thus there will be a trade-off between increased specificity of ligation at high temperature, and increased yield of ligation at low temperature due to absence of end-fraying.

A third temperature effect arises from the cooperativity of binding of adjacent oligonucleotides to a template, and may also be significant. Consider a set of oligonucleotide probes which binds to the target DNA strand. If "p" is the probability of a single ligation event, then $(p)^N$ is the probability of N independent ligation events. If there is a 10% yield for each independent ligation event (A/B, B/C, C/D, D/E) in the reaction of FIG. 2, then the combinatorial yield of final product should be $(10\%)^4 = 0.01\%$. This is a very low overall yield, and implies that, all else being equal, multiple-ligation products should be quite difficult to detect by a fluorescence-based gel method.

However, a cooperativity effect occurs in the ligation reactions of the invention, to greatly increase the overall yield of a multiple ligation reaction. Cooperativity in the binding of adjacent oligonucleotides to a single-stranded template has been observed for a variety of different sequences (Mesner & Hockensmith, 1992; Kotler et al., 1993; Kaczorowski & Szybalski, 1994). Because of this cooperativity, the overall yield of a multiple ligation reaction typically will be much higher than predicted from a simple combinatoric probability model.

Because of this cooperativity, multiple rounds of ligation (in a thermal cycling format) and in the absence of mismatches between probes and target causes virtually all oligonucleotides to be driven into the fully-ligated form, because the cooperativity parameter $\omega > 1$. In contrast, when one oligonucleotide within the probe set is mismatched, the cooperativity effect will be offset. This oligonucleotide will not ligate efficiently to its neighbors, and the overall yield of final ligation product will be low.

This cooperativity in binding of adjacent oligonucleotides to a template probably is due to a stacking interaction between the terminal bases of the adjacent oligonucleotides. Because base stacking involves a release of enthalpy, there should be a significant negative temperature dependence to the cooperativity parameter, with higher temperatures generally giving rise to a decrease in cooperativity (by analogy to Eq. 2A–2C).

Taking into consideration the aforementioned temperature effects, we have determined that a good compromise temperature at which to begin optimization is usually somewhat below (i.e., 15 to 25° C. below) the average estimated Tm for the oligonucleotide probe set as computed using equation (1). For many ligases, the trade-off would argue for a ligation temperature about 20° C. below the average Tm of the oligonucleotide probes (see Eq. 1 and FIG. 4), or around 60° C. when using typical ligation conditions of 10 nM concentration of each probe and of the target.

The hybridization/ligation buffer can also play an important role in determining the stringency of the hybridization conditions and the activity of the ligase. In general, a suitable buffer contains 10 mM $Mg^{2+}$ and is buffered to pH 7–8. Constituents such as monovalent salts or spermidine which increase the stringency of the ligation can also be employed provided that they do not interfere excessively with the activity of the selected ligase.

The pH of the buffer may play an important role in the ability to discriminate some mismatches using the assay of the invention. This is the case because the destabilization of the duplex caused by mismatches is due at least in part to a disruption of hydrogen bonding within the mispair itself Thus, Brown et al. (1990) determined that the destabilizing influence of certain point-mismatches (A:C and C:C) exhibits a pH-dependence. At acid pH, these particular mispairs are more stable than the corresponding true base pairs, due to appearance of protonation-dependent hydrogen bonding. Thus, the pH of the ligation buffer may be a critical variable using the assay of the invention to detect some mutations, for reasons in addition to any direct effect on DNA ligase activity. As a result, the pH of the buffer will generally be 7 to 8. However, it may prove advantageous to set the pH outside this range to detect certain mutations.

Figure 5A:
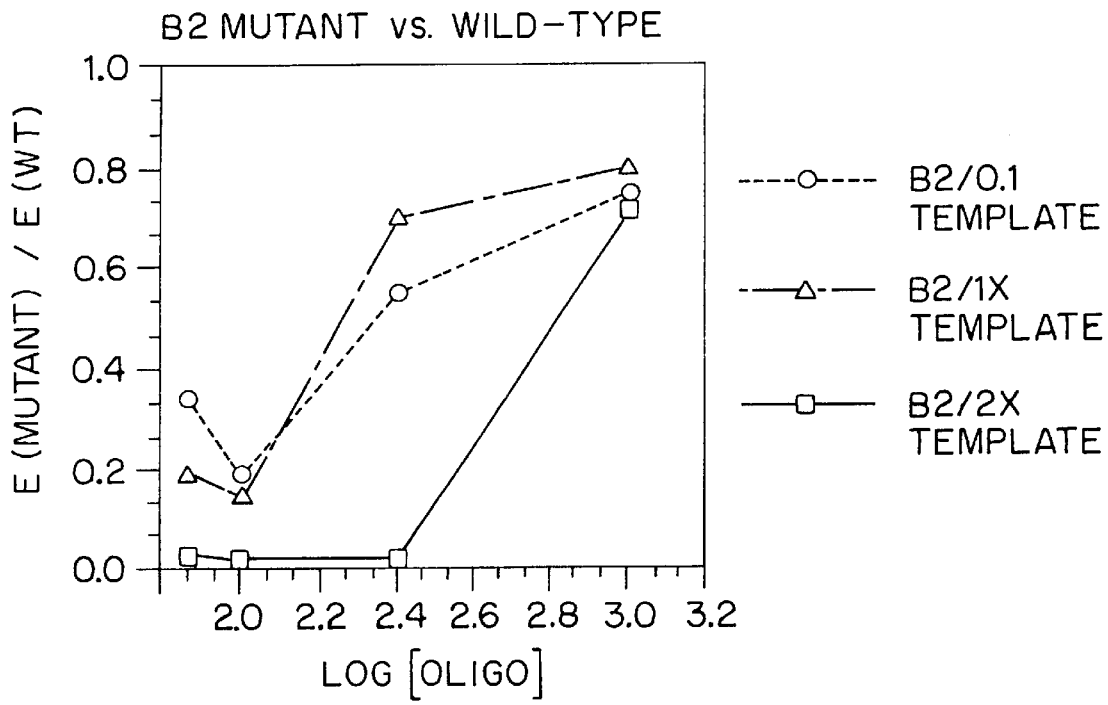
FIGS. 5A–5C show the effect of varying probe and template concentration on the ability to identify mutants using the method of the invention.
Figure 5B:
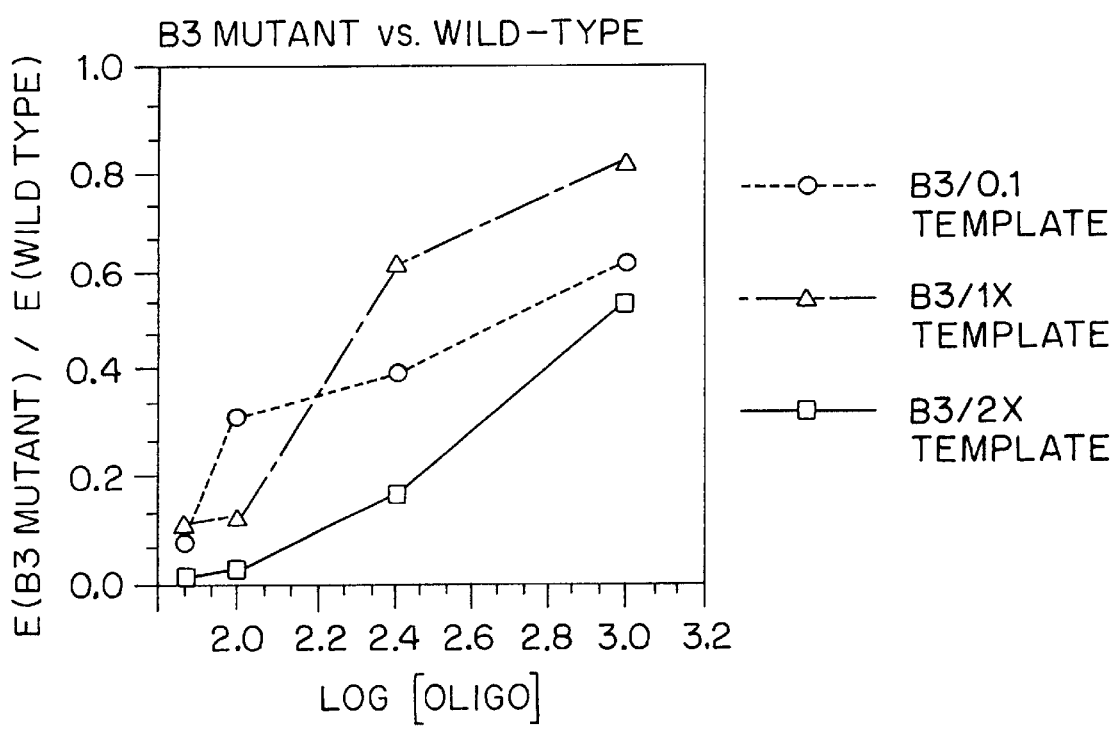
Figure 5C:
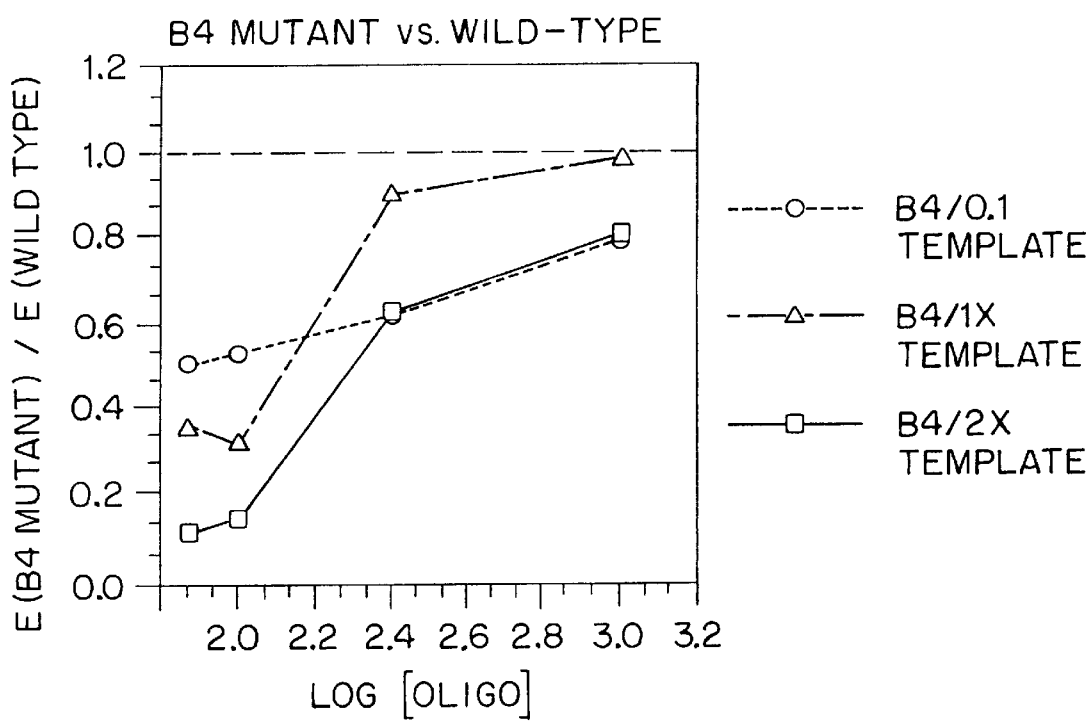

Another factor which may affect the clarity of the results is the concentration of oligonucleotide probes in the ligation reaction. The ratio of the amount of full length product obtained using a mismatched oligonucleotide set to the amount of full length product obtained using a perfectly matched oligonucleotide set ("ABCDE(mutant)/ABCDE (wild type)") reflects the amount of discrimination which can be obtained using the method of the invention. FIGS. 5 A, B and C depict such ratios for a five probe set based upon the exon 1 of the human KRAS gene (see Example 6). In this example, a single point mutation is introduced at varying nucleotide positions within the second (B) probe. As shown, the ratio increases at higher concentrations of probes, such that using concentrations which exceed 1000 femtomoles of probes per 10 μl reaction mixture (100 nM each probe) leads to a loss of the ability to discriminate mutants from non-mutants when a single point mutation is involved. This may be due to a mass action effect, whereby incompatible oligonucleotides are routinely incorporated into the final product making identification of the mutations difficult. Regardless of the mechanism, however, the decrease in discrimination means that the method of the invention must be performed at sufficiently low concentrations of probe, for example from 100 to 250 femtomoles per 10 μl reaction mixture (10 to 25 nM) in the case of single point mutations, to permit a suitable level of discrimination between mutant and non-mutant species.

A further factor in improving discrimination in the method of the invention which can be derived from the data shown in FIG. 5 involves the concentration of template. As shown, the best discrimination is always achieved at the highest template concentration. Thus, increased discrimination can be obtained by increasing the concentration of the DNA in the sample, for example by PCR amplification.

After allowing time for hybridization to occur (generally from 1 to 5 minutes), a ligase is added and an attempt is made to ligate the oligonucleotide probes together at the hybridization conditions. Ligation will fail, or at least will be inefficient, for any oligonucleotide probe that spans a mismatch site, because this oligonucleotide will preferentially be melted at the ligation temperature. A "ligation gap" therefore will persist at the position which corresponds to the oligonucleotide containing the mutation.

Suitable ligases for use in the method of the invention are those which are cormpatible with the elevated-temperature hybridization conditions necessary for any given set of probes and which display minimal activity in undesirable non-template-directed ligation. One particular ligase which is generally useful in the elevated temperatures required for many probes sets is the DNA ligase from *Pyrococcus furiosisus* which is available from Stratagene and which is described in Marsh et al., "*Pyrococcus furiosus* DNA Ligase and the Ligase Chain Reaction," Strategies (Stratagene) 5: 73–76. (1992). Other thermostable enzymes such a Q-beta ligase may also be useful in the present invention.

As reflected in FIGS. 2 and 3, either the oligonucleotide probes or the target strand are labeled to provide a detectable product. Preferably, the first and last probes in sequence or both ends of the target strands are labeled with different labels to avoid complications which may arise when a mutation appears in the region spanned by one of the terminal probes. Nevertheless, the use of a label at only one end can be successfully employed, as can a single label at both ends, or even labels attached to each probe species. It will be appreciated, however, that the use of a single label at one or both ends of the expected full length ligation product provides less information than the use of two distinctive labels. Specifically, the use of the same label at both ends of the ligation product may make it difficult to identify the location of the mutation unambiguously because it may be unclear which labeled probe is closest to the mutation.

There are numerous types of labels known for use in detecting oligonucleotide fragments, and any of these labels which does not interfere with the hybridization and ligation steps of the invention can be employed. This will include radiolabels, colored labels, fluorescent labels, optically active labels, and enzymatic chromogenic or fluorogenic labels. Preferred labels are fluorescent labels such as fluorescein, rhodamines, infrared dyes such as IR-132 or IR-144 (Kodak, Rochester, N.Y.) and cyanine dyes such as Cy5.5 (Amersham Int'l, Cleveland). Labels such as biotin which can act to couple a detectable label or to capture the ligation product may also be employed.

The probes used in the invention may also need to be modified to permit them to act as substrates for the ligase enzymes. DNA ligases requires the presence of a 5'-phosphate group on the second member of each pair of adjacent oligonucleotides which are to be ligated together. Thus, the 5'-end of all but the 5'-terminal probe may (depending on the synthetic technique employed in making the probes) need to be covalently modified to incorporate such a group.

The final step in the method of the present invention is determination of the size of ligation products, and comparison of the size(s) or size distribution with the expected result if the target gene or gene fragment had the wild-type sequence. This determination step will generally involve separation of the ligation products, for example by gel electrophoresis, and then detection of the separated ligation products.

The detection of the separated ligation products can be based upon an inherent property of oligonucleotides such as optical activity, as described in commonly assigned U.S. patent application Ser. No. 08/387,272 which is incorporated herein by reference. Detection can also be accomplished through the addition of a material which permits visualization of the oligonucleotide positions following separation. An example of this would be the use of ethidium bromide stain to visualize DNA fragments within a gel in the embodiment shown in FIG. 3 where double stranded products can be readily evaluated.

Preferably, however, the ligation products are detected using a fluorescent label which is incorporated into either the probes or the target strand prior to the ligation reaction. Detection of such labels can be performed in real time during separation, for example using an instrument of the type described in commonly assigned U.S. patent application Ser. No. 08/353,932 and the continuation-in-part thereof filed as PCT Application No. PCT/US95/15951, or U.S. Pat. Nos. 5,630,523, 5,171,534 or 5,192,412 all of which are incorporated herein by reference.

The method of the present invention is advantageously practiced for any given gene or gene fragment using a kit containing three or more, and preferably five or more probes which have sequences which are perfectly complementary to and hybridize with sequential and contiguous portions of the wild-type sequence of the gene or gene fragment. In preferred kits, at least one of the probes will be labeled with a fluorescent label. Such kits may also contain, in packaged combination, one or more of the following: a hybridization/ligation buffer; a ligase enzyme; amplification primers for amplification of the gene or gene fragment; and amplification reagents.

The following examples provide further details concerning the practice and implementation of the invention, but are not intended to limit the scope of the invention as defined by the claims.

EXAMPLE 1

Fluorescent Labeling of Terminal Oligonucleotides

A fluorophore of one type (designated "F1" in FIG. 2) is added to the 5'-terminus of the first oligonucleotide of the probe set. Greatest flexibility in the choice of label can be obtained by using a two-step reaction scheme in which: (i) an oligonucleotide is first synthesized with a 5'-aliphatic amino group (Nelson et al., 1989; 1992), and then (ii) the amino group is coupled to an activated dye precursor (Smith et al., 1985; 1987). This approach allows use of any fluorophore which can be suitably activated.

The method of the invention can be made more robust by increasing the amount of information that it generates. This can be achieved by putting a second fluorophore of a different type (designated "F2") on the 3'-terminus of the last oligonucleotide of the probe set. In this case, two ladders of fluorescently end-labeled ligation products will be generated in the assay. The ladders will be labeled on opposite ends.

The 3'-terminus of the last oligonucleotide can be labeled in two ways. (i) Terminal deoxynucleotidyl transferase may be used to add a single extra fluorescently-labeled nucleotide from a fluorescent dideoxy(NTP) precursor (Trainor & Jensen, 1989; Dirks et al., 1991; Figeys et al., 1994). (ii) A fluorescently-labeled controlled-pore-glass (CPG) reagent may be used to initiate the synthesis of the oligonucleotide at the 3'-end, using standard phosphoramidite chemistry (Nelson et al., 1989, 1992). After deprotection, the 3'-terminus will contain a fluorescent label. All necessary reagents for either 3'-labeling procedure are available commercially (Applied Biosystems, Inc, Boehringer, Clontech).

EXAMPLE 2

Addition of Phosphate Group to 5'-end of Oligonucleotide Probes

To render the downstream oligonucleotides probes ligatable with DNA ligase, a phosphate group must be attached to the 5'-end of each one. An efficient phosphorylation can be done using T4 polynucleotide kinase and ATP (Sambrook et al., 1989). We typically conduct a 60 $\mu$l reaction with 3.6 nmol oligonucleotide, 100 nmol ATP and 50 U of T4 polynucleotide kinase. The reaction is incubated for 45 min at 37° C. It is extracted once with phenol/chloroform, and then extracted with ether. Residual ether is removed by heating at 37° C. for 10 min. The phosphorylated oligonucleotide does not have to be purified further.

The efficiency of the 5'-phosphorylation reaction can be assessed by analytical HPLC, using a 125×4 mm silica-based anion exchange column (100 Å, 5 $\mu$m) flowing at 1 ml/min in buffer A=20 mM sodium phosphate (pH 5.5), with a 1%/min gradient of buffer B=A+1 M KCl (Wickstrom, 1995). Under these conditions, the phosphorylated oligonucleotide elutes around 4 minutes, and the unphosphorylated starting material elutes around 23 minutes.

EXAMPLE 3

Preparation of Target DNA Strand

Because the presence of the non-target DNA strand may exert an inhibitory effect on ligation in the method of the present invention, it is advantageous to purify the target DNA strand away from its complementary strand, before conducting the assay. While any method for purification can be used, two specific techniques which are useful are asymmetric PCR, and biotin/streptavidin capture.

Asymmetric PCR: This technique is used to generate an excess of one DNA strand (Gyllensten & Erlich, 1988; Innis et al., 1988; Kreitman & Landweber, 1989; Wychowski et al., 1990; Wilson et al., 1990, Kadowaki et al., 1990; Allard et al., 1991). If unequal concentrations of primers are used in PCR, then the PCR will display two phases. In the first phase, double-stranded DNA will be produced, in an amount that increases exponentially with the number of cycles. This will continue until the limiting primer is exhausted. In the second phase, there will be a continued production of one strand, due to repeated rounds of primer-extension from the non-limiting primer. The amount of this primer-extended product will increase linearly with the number of cycles.

Biotin/Streptavidin Capture: A genomic PCR product is generated using one 5'-biotinylated primer and one unmodified primer. The biotin moiety should be attached to its DNA strand by a spacer, to reduce the effect of stearic hindrance between the PCR product and its solid-phase "capture reagent" (a streptavidin-conjugated bead). The PCR product is captured on the solid phase, and the non-biotinylated strand is then released by an NaOH wash (Uhlen et al., 1994;

Dynal, 1995). Either the captured DNA strand (on the beads) or the released DNA strand (in the eluent) can be evaluated for mutations by the assay method of the invention. In other words, it is possible to designate either the captured strand or the eluted strand as the target (T). However, the assay may be more reliable when the bound DNA strand is used as target, because it can be difficult to precisely adjust the pH of the released strand after its elution with NaOH (Dynal, 1995).

EXAMPLE 4

Hybridization and Ligation of the Probe Set

The selected oligonucleotide probes are mixed in equimolar concentration with each other and with the target DNA strand, with probe concentrations generally being in the range of from 0.5–40 nM, preferably 10 to 25 nM. The optimal concentration within this range will depend on the stringency of the hybridization conditions, and the sensitivity of the detection system employed (which is to some extent label dependent). Too low a concentration will lead to inefficient hybridization at the assay temperature, and will make fluorescent-based gel detection difficult. Too high of a concentration will lead to the loss of specificity noted in FIG. 5.

After hybridizing the set of oligonucleotide probes to the target, ligation is attempted at a temperature which lies somewhat below Tm (the average melting temperature of the oligonucleotide probe set). For a solution of perfectly-matched 21-mer probe and its target, each at 10 nM concentration in a typical ligation buffer containing 10 mM $Mg^{2+}$, 20 mM Tris HCl, 20 mM KCl, 0.1% NP40, 0.1 MM rATP, 1 mM DTT, Equation (1) can be used to estimate that Tm≈90° C. for this sample. 2 units of DNA ligase from *Pyrococcus furiosus (Stratagene)* is added per 10 μl reaction mixture, and 8 cycles of ligation are conducted, 15 minutes per cycle, at a temperature of 65 to 67° C.

EXAMPLE 5

An assay for mutations is conducted using the test format shown in FIG. 3. A set of oligonucleotide probes is designed, each ~20 nt long, to exactly complement the wild-type sequence, with no mismatches, gaps or overlaps. Against the wild-type template, the set of test oligos should be fully ligatable to produce a significant amount of full-length ligation product. The lengths of the oligonucleotides are adjusted to equalize their estimated thermodynamic stabilities and melting temperatures.

A genomic PCR product is generated using one 5'-biotinylated primer and one normal primer. The biotinylated single strand of the PCR product is purified using streptavidin-conjugated beads. In this case, the non-captured single-strand of the PCR product (i.e. the flow-through strand) is to be scanned for the presence of new uncharacterized mutations.

The 5'-terminus of the flow-through strand (T) has been pre-labeled with fluorophore F1. To increase the information content of the data, the 3'-terminus of this strand may also have been pre-labeled with fluorophore F2 using a dye-labeled dideoxy NTP and terminal transferase.

The set of oligonucleotide probes is mixed with the template in equimolar amounts with other and the template. Next, ligation is attempted at somewhat below Tm, the average equilibrium melting temperature of the set of oligonucleotide probes. Thermostable DNA ligase from *Pyrococcus furiosus* is used in amounts of from 2 to 4 units per 10 μl reaction.

The ligated complex is passed through a gel-filtration column. The oligonucleotide probe corresponding to the mismatch position (M≈20×330 g/mol=6,600 g/mol) is retained on the column. The flow-through product will consist of a duplex product containing an about 20 nucleotide single-stranded gap. The single-stranded gap will span the site of the mutation. Because of the large difference in molecular weight and frictional properties, the duplex product (M≈180×330 g/mol=59,400 g/mol) will be easily separated from the mismatched, unligated 20-mer that spans the mutation (M=20×330 g/mol=6,600 g/mol).

The flow-through complex is digested with S1 or P1 nuclease. Digestion conditions are adjusted to maximize the nuclease's preference for digesting the single-stranded gap instead of flanking duplex sequence (Potapenko & Obukhova, 1992; Box et al., 1993). An S1 or P1 column may perhaps be employed (Gite & Shankar, 1993). The released DNA fragments, each bearing a fluorophore (F1 or F2), can be sized on a gel. The sizes of these two released end-labeled fragments will allow the site of the mutation to be localized to±N/2 nucleotides (±half the length of the unhybridized oligonucleotide).

EXAMPLE 6

A purified single stranded DNA sequence ("KR") representing a 61nt fragment of human K-ras was synthesized on an Expedite™ Nucleic Acid Synthesis System (Millipore, Inc.) using reagents standard for that system. The DNA sequence of the synthesized oligonucleotide was as follows:

```
                                        SEQ ID NO: 1
   TATCGTCAAG GCACTCTTGC CTACGCCACC AGCTCCAACT

ACCACAAGTT TATATTCAGT C
```

Figure 6:
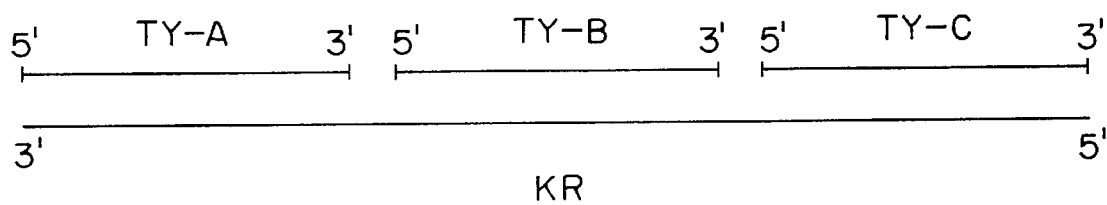
FIG. 6 shows a three probe set for evaluation of the K-ras gene.
Figure 7:
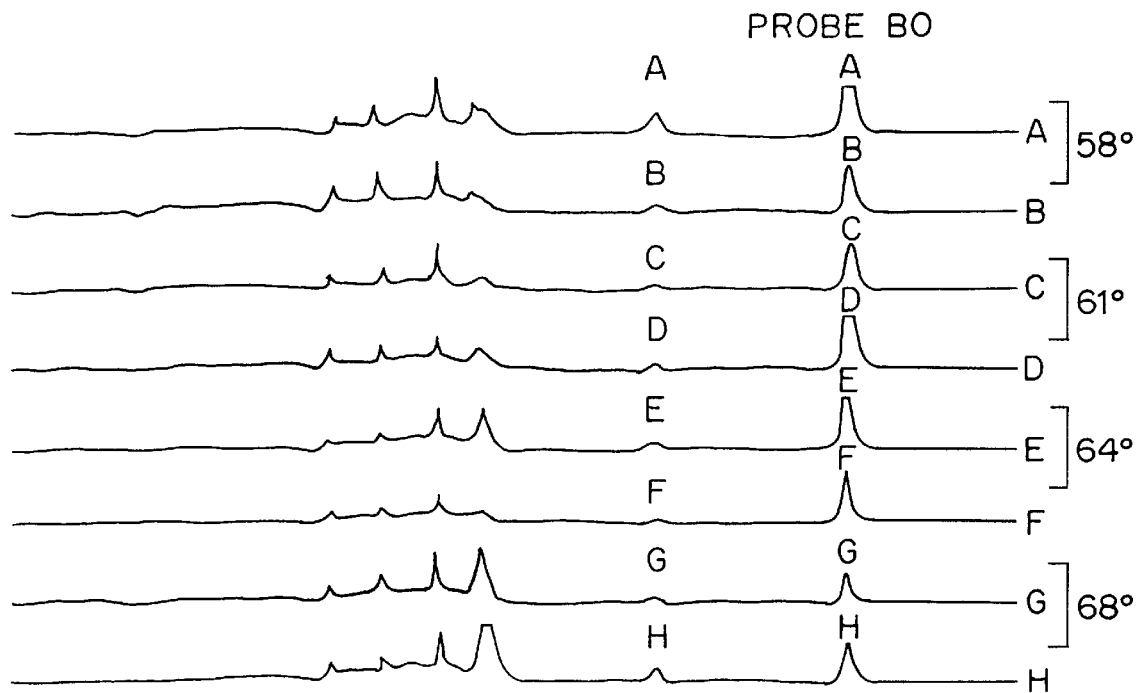
FIGS. 7 to 11 show the results of a mini-assay using a three probe set for the K-ras gene.

Three shorter oligonucleotide probes complementary to KR, TY-A, TY-B0, and TY-C were prepared as illustrated in FIG. 6 such that upon hybridization to KR, the probes would form a contiguous, non-overlapping complement to KR. In other words, the 5'-end of the middle oligonucleotide TY-B0 would lie ligatably juxtaposed to the 3'-end of the first oligonucleotide, TY-A, and the 3'-end of TY-B0 would lie ligatably juxtaposed to the 5'-end of TY-C. The DNA sequence of these oligonucleotides was as follows:

```
TY-A     GACTGAATAT AAACTTGTGG TAG    SEQ ID No.: 2

TY-B0    TTGGAGCTGG TGGCGTAG           SEQ ID No.: 3

TY-C     GCAAGAGTGC CTTGACGATA         SEQ ID No.: 4
```

A further set of oligonucleotides similar to TY-B0 but each containing a single point mutation were also synthesized. The point mutations in TY-B1, TY-B2, TY-B3 and TY-B4 were designed prevent the oligonucleotide from hybridizing with exact complementarity to KR. From FIG. 6, it can be seen that TY-B1 results in a mismatch at the 3' end of TY-B1, which is the site of ligation. TY-B2 represents a mismatch 4 nt from the ligation site. TY-B3 represents a mismatch 7nt from the ligation site and TY-B4 represents a mutation 10 nt from the ligation site, approximately in the middle of the oligonucleotide:

```
TY-B1    TTGGAGCTGG TGGCGTAC*    SEQ ID No.: 5
```

```
                  -continued
TY-B2    TTGGAGCTGG TGGCC*TAG    SEQ ID No.: 6

TY-B3    TTGGAGCTGG TC*GCGTAG    SEQ ID No.: 7

TY-B4    TTGGAGCTC*G TGGCGTAG    SEQ ID No.: 8
```

*marks the point mutation relative to TY-B0

Oligo Modification

Prior to the ligation reaction, the synthesized oligonucleotides were modified as follows:

TY-A was fluoresceinated at the 5'-end according to the standard method of the Expedite (TM) Nucleic Acid Synthesis System. TY-B0, TY-B1, TY-B2, TY-B3, TY-B4 and TY-C were phosphorylated at their respective 5' ends in order to become ligation competent. For the phosphorylaton step, the final 60 microlitre reaction volume consisted of:

100 nmoles ATP 3.6 nmoles of selected oligo

50 U T4 polynucleotide kinase (New England Biolabs)

1X concentrated polynucleotide kinase buffer (New England Biolabs)

final [ATP] 1.2 mM final [oligo]=60 uM final [ATP/oligo] ratio=20:1 final [PNK]=0.82 U/microlitre

The reaction mixture was incubated for 45 min at 37 degrees C. After phosphorylation, the enzyme was heat killed, and extracted with one phenol/chloroform extraction and a further ether extraction. The resulting stock solution of oligo was approximately 120 pmol/micro-litre, which is approximately 1000X required concentration for later reactions.

Sequential Ligation Assay for Mutations

All oligonucleotides were diluted to 10 nM. The following components were combined:

1 microlitre KR 1 microlitre TY-A (fluoresceinated)

1 microlitre TY-B0 or TY-B1 or TY-B2 or TY-B3 or TY-B4 (phosphorylated)

1 microlitre TY-C (phosphorylated)

4 microlitre water 1 microlitre 10× Pfu ligase buffer (Stratagene)

The above components were mixed well and heated to 95 degrees C., whereupon 1 microlitre Pfu DNA ligase (4 Units) (Stratagene) was added. An oil overlay was added to the reaction mixture.

The reaction mixture was then subjected to the following thermal cycling:

15 mins at X degrees Celsius 30 seconds at 94 degrees Celsius for a total of eight cycles, where X is 58 degrees, or 61 degrees or 64 degrees or 68 degrees.

After the final 94 degree incubation, the reaction solution was maintained at 94 degrees until an equal volume of loading buffer consisting of 100% formamide with 5 mg/ml dextran blue was added to the reaction solution. The samples were then loaded on a Pharmacia A.L.F. automated electrophoresis apparatus and examined.

FIG. 6 shows results of reactions with the TY-B0 reaction mixture. The full 60 nt ligation product is quantitatively far in abundance over shorter ligation products. The ratio of full ligation products to incomplete ligation products varies from 3.0 to 13.6. The highest ratios were obtained at the 64 degree ligation cycling temperature.

Figure 8:
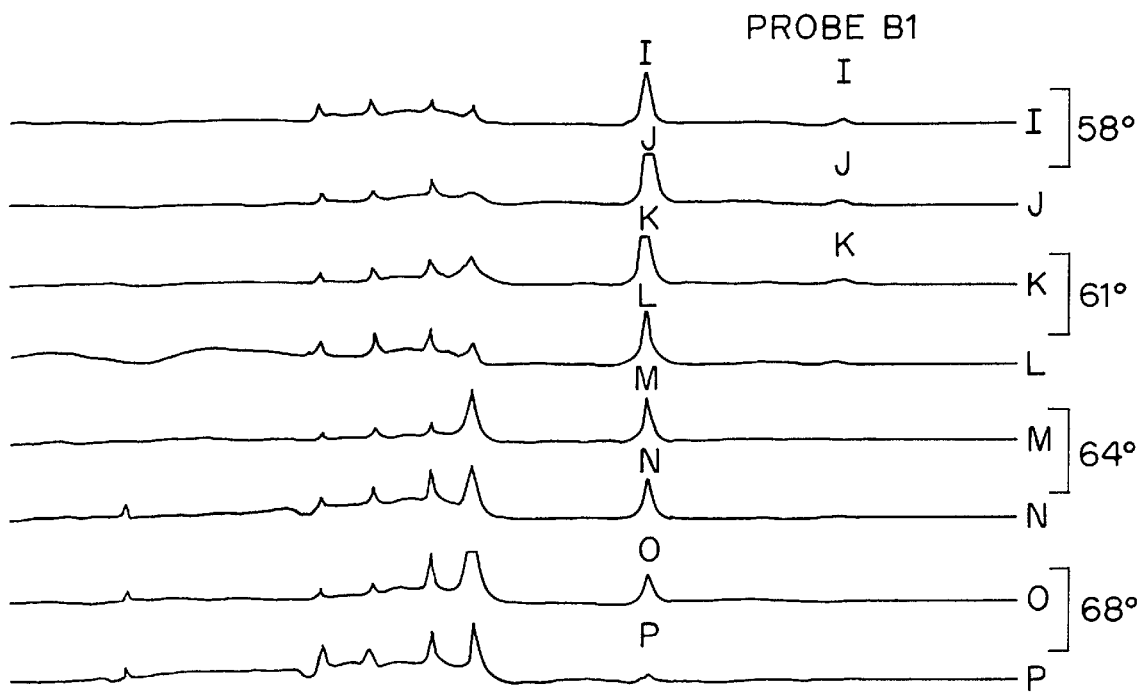
Figure 9:
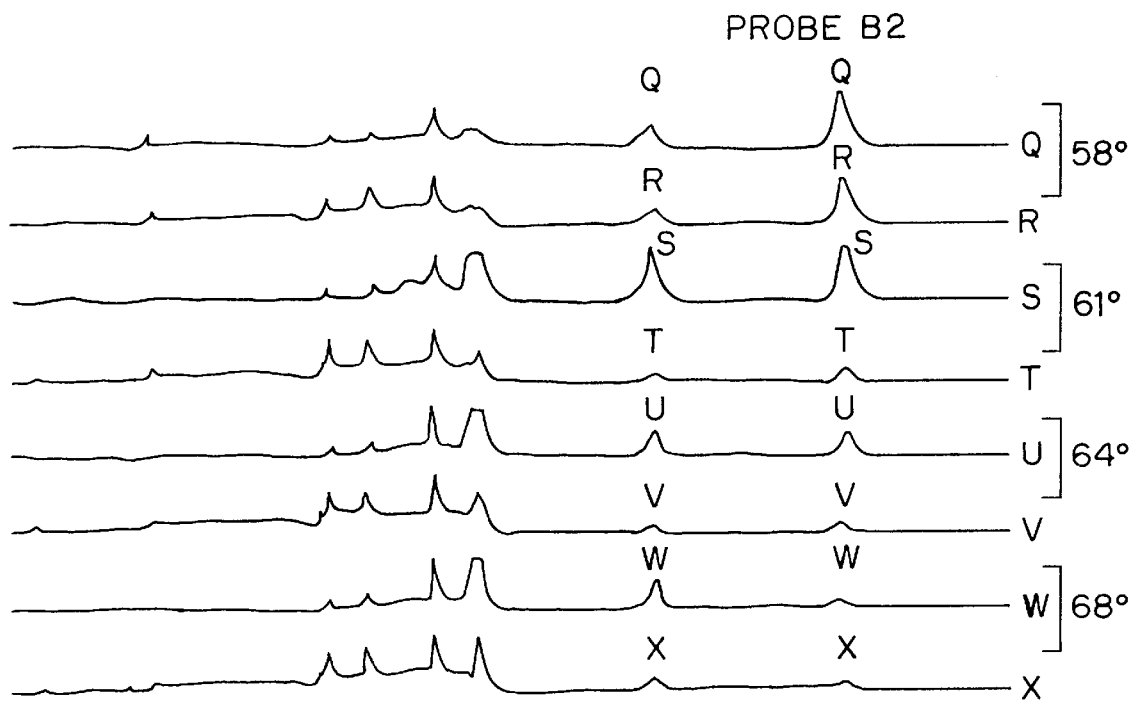
Figure 10:
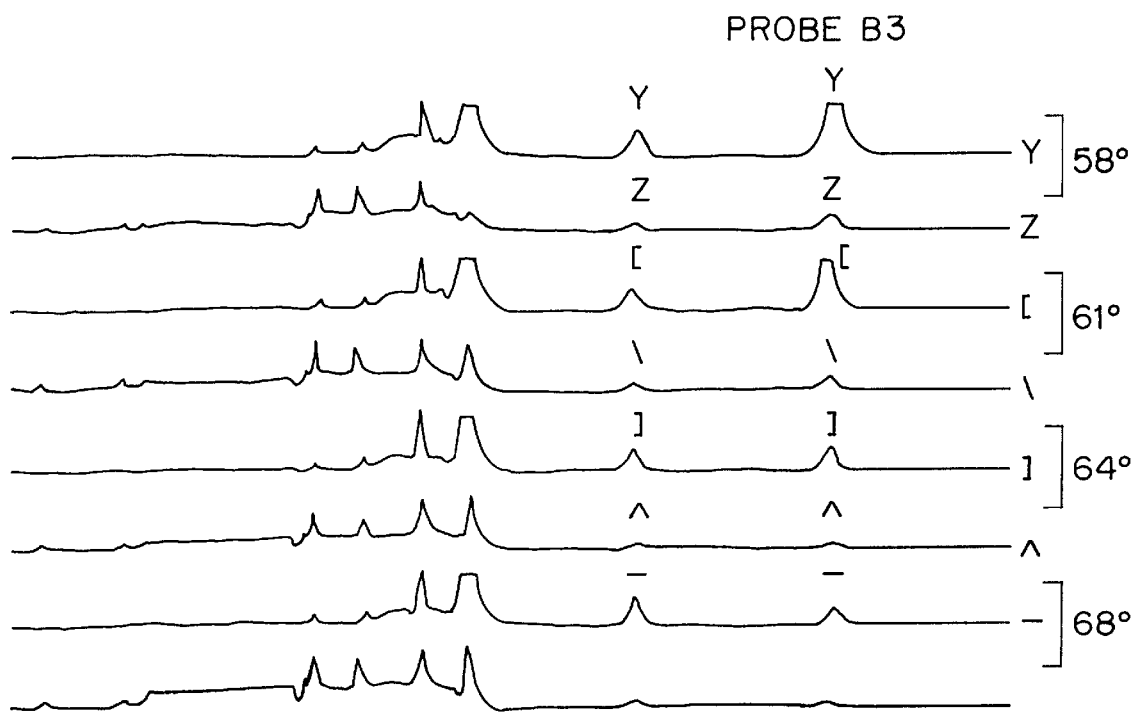
Figure 11:
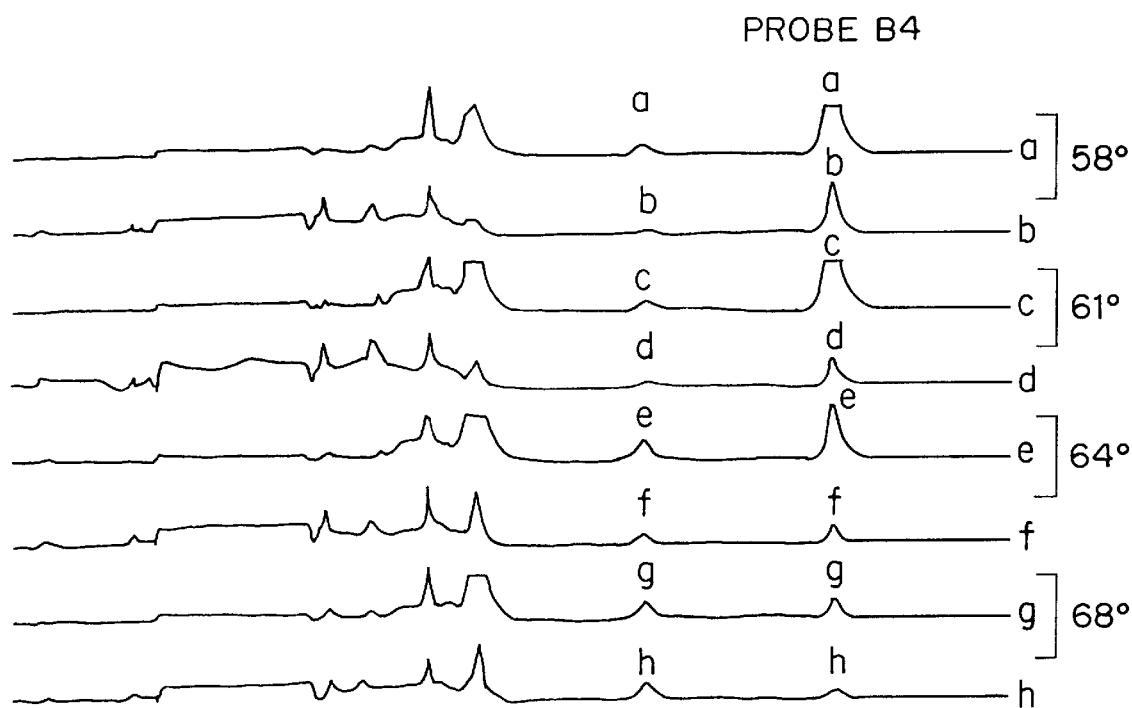
Figure 12:
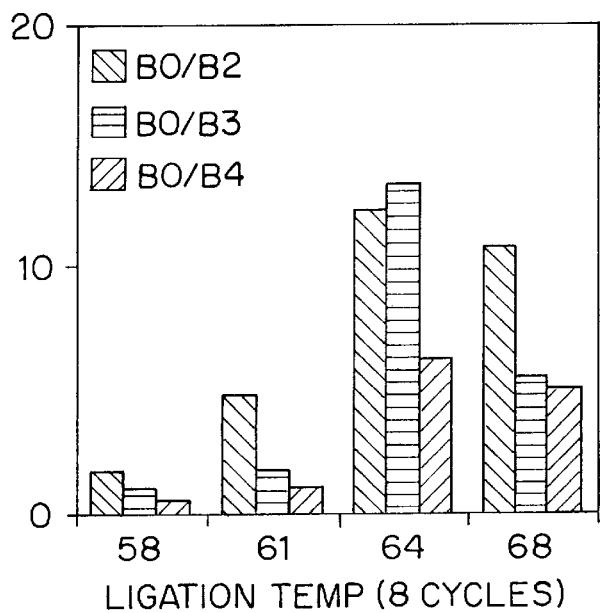
FIG. 12 summarizes the results of mini-assays using three oligonucleotide probe sets at various reaction conditions.

FIGS. 8–11 demonstrate that when mismatched oligonucleotides are employed in a sequential ligation assay, the ratio of incomplete reaction products increases sharply relative to the complete reaction products. In FIG. 8, the 3' end nucleotide mismatch of TY-B1 virtually excludes the generation of a 60 nt fragment. The highest temperatures are the most effective at preventing full length ligation, presumably because of the increased stringency of hybridization. FIGS. 9–11 show that where the mutation is more internal to the oligonucleotide, it does allow for some generation of the full length ligation product. However, the ratio of results does not approach the ratio of products when no mutation is present, except at the lowest ligation temperatures. (FIG. 12)

It should be noted that this example format differs from what would be the normal assay format, in that a variable set of primers was used rather than a potentially mutated gene or gene fragment. The thermodynamics and kinetics of the binding of the fragments, however, is sufficiently similar, such that this provides a valid model which demonstrates the operability and utility of the invention.

EXAMPLE 7

Exon #1 of the human kras1p gene was analyzed for the presence of mutations using the methods of the invention. Codon 12 of this gene, which occurs in exon #1, is found to be mutated in a wide variety of human cancers (see e.g. Pulciani et al., 1982; Yanez et al., 1987; Burmer & Loeb, 1989). Exon #1 is 111 base-pairs long, and has the following wild-type sequence:

```
                                                 [SEQ ID NO: 9]
  ATGACTGAAT ATAAACTTGT GGTAGTTGGA GCTGGTGGCG

TAGGCAAGAG TGCCTTGACG ATACAGCTAA TTCAGAATCA

TTTTGTGGAC GAATATGATC AACAATAGA G
```

An outer primer-pair may be used first against human genomic DNA to amplify a 162 base-pair fragment, which contains the entire exon #1 (Orita et al., 1989). The sequence of the outer primers are:

```
  KA-13.1

GGCCTGCTGA AAATGACTGA        [SEQ ID NO.: 10]

KA-13.2

GTCCTGCACC AGTAATATGC        [SEQ ID NO.: 11]
```

A second nested PCR is then performed, to amplify a 106 base-pair fragment which spans from position 3 to position 108 of exon #1. The primers for the internal PCR are:

```
  KA-12

GACTGAATAT AAACTTGTGG        [SEQ ID NO.: 12]

KB-12

TATTGTTGGA TCATATTCG         [SEQ ID NO.: 13]
```

Oligonucleotide probes for use in the ligation assay of the invention were designed originally with a nominal length of 20 nucleotides. These lengths were then adjusted slightly to equalize their thermodynamic properties ($\Delta G°_f$ values, Tm values, G+C contents) by using the commercially available "Oligo" program (Rychlik & Rhoads, 1989). The resulting probes are shown in Table 1.

TABLE 1

| PROBE | LENGTH | SEQUENCE | POS IN EXON 1 |
|---|---|---|---|
| A | 23 | 5' F1-GAC TGA ATA TAA ACT TGT GGT AG-3' OH SEQ ID NO: 2 | 3–25 |
| B | 18 | 5' p-TTG GAG CTG GTG GCG TAG-3' OH SEQ ID NO: 3 | 26–43 |
| C | 20 | 5' p-GCA AGA GTG CCT TGA CGA TA-3' OH SEQ ID NO: 3 | 44–63 |
| D | 23 | 5' p-CAG CTA ATT CAG AAT CAT TTT GT-3' OH SEQ ID NO: 14 | 64–86 |
| E | 23 | 5' p-GGA CGA ATA TGA TCC AAC AAT A-F2 3' SEQ ID NO: 15 | 87–108 |

The thermodynamic properties of this set of probes were computed with the "Oligo"program and are shown in Table 2. There are two important points. (1) $\Delta G°_f$ and Tm values for the different oligonucleotides are roughly equal. The oligonucleotide that contains the mutation is designed to be slightly less stable than the rest. (2) There are no highly stable hairpins or internal duplexes in either the template strand (T) or in any of the probe oligonucleotides.

TABLE 2

| PROBE | $\Delta G°_f$ (kc/m) | Tm (° C.)* | max hairpin | max duplex |
|---|---|---|---|---|
| A | −35.6 | 62–66 | none | −4 kc/m (4 bp) |
| B | −36.8 | 58–69 | none | −6.3 kc/m (4 bp) |
| C | −37.1 | 60–68 | −1.0 kc/m | −5.4 kc/m (4 bp) |
| D | −38.5 | 60–65 | none | −5.3 kc/m (4 bp) |
| E | −38.1 | 60–66 | −0.5 kc/m | −4.7 kc/m (4 bp) |

*estimated as range from two different (G + C)-based algorithms.

Probe B overlaps with codon 12 which is the region of the gene which is known to contain mutations of diagnostic or clinical significance. This probe is designed to be shortest, so that the effect of mismatch will be maximized.

EXAMPLE 8

Figure 13:
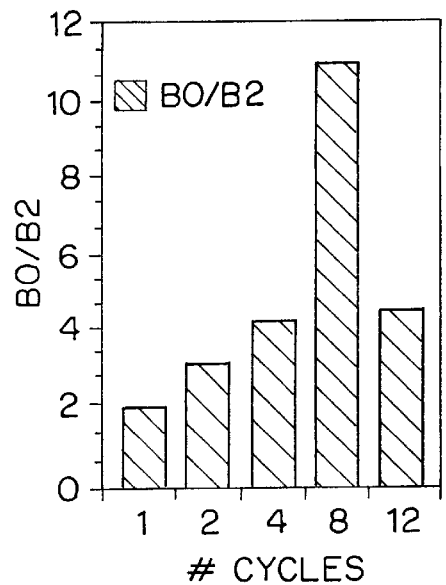
FIG. 13 summarizes results of assays performed at various reactions conditions.

The mini-assay of Example 6 was repeated with variation of ligase concentration, the number of thermal cycles, and whether "hot start" or "cold start" reaction conditions were used. Results of this survey are shown in FIG. 13. As the number of thermal cycles is increased from 1 to 8, there is a great improvement in discrimination. However, above 8 cycles this trend is reversed. We observe no significant effect of ligase concentration, over a 4-fold range. We also find that "hot start" versus "cold start" is not important.

EXAMPLE 9

Assay for Mutations in Exon 8 of RB 1 Gene

The method of the invention was used to assay for mutations of the retinoblastoma susceptibility (RB1) gene. Sample DNA was amplified by symmetric amplification for 33 cycles using primers flanking exon 8 of the RB1 gene using Taq polymerase. The 3'-primer was biotinylated. The 5' primer was labeled with a fluorescent label, Cy 5.5, to enable detection of the PCR product in the assay.

Ten ul of streptavidin-coated beads (Dynal) were washed with 40 ul of 2× BW buffer (Binding/Washing buffer: 10 mM Tris pH 7.5, 1 mM EDTA, 2M NaCl) according to the manufacturer's instructions. The supernatant was removed using a magnetic rack and discarded. 25 ul of 2× BW buffer and 25 ul of PCR product were added to each aliquot of beads, and incubated with occasional and gentle mixing. The supernatant was again separated using a magnetic rack and discarded. The beads, having the biotinylated PCR product attached were washed with 40 ul 2× BW buffer then 40 ul 1× TE and then resuspended in 10 ul water for use in the assay of the invention. It is important to wash the beads carefully, since residual Taq polymerase activity can interfere with the assay.

The assay of the invention was then performed using the oligonucleotides shown in Table 3. These oligos are designed to span the entirety of wild-type RB1 exon 8 without gaps, overlaps, insertions, deletions or mismatches. Each has a length of about 20 bases, and was chosen so that oligos B–I all have approximately equal annealing temperatures and to minimize formation of hairpins and duplexes.

TABLE 3

| Oligo [Seq Id #] | Sequence | Length | $\Delta G_f°$ | Tm (° C.) | Stack Alg | hair- pin | du- plex |
|---|---|---|---|---|---|---|---|
| A | TTTACCACTT | | | | | | |
| [16] | TTACAGAAC | | | | | | |
| B | AGCTGTTATA | 19 | −32.5 | 50.0–58–9 | 50.8 | +1.2 | −7.8 |
| [17] | CCCATTAAT | | | | | | |
| C | GGTTCACCTC | 16 | −29.0 | 50.0–62.4 | 51.0 | −0.4 | −6.8 |
| [18] | GAACAC | | | | | | |
| D | CCAGGCGAGG | 14 | −29.2 | 50.0–62.6 | 52.6 | none | −3.6 |
| [19] | TCAG | | | | | | |
| E | AACAGGAGTG | 15 | −29.2 | 48.0–61.1 | 52.5 | none | −9.5 |
| [20] | CACGG | | | | | | |
| F | ATAGCAAAAC | 20 | −32.8 | 50.0–58.0 | 51.9 | +1.5 | −4.2 |
| [21] | AACTAGAAAA | | | | | | |
| G | TGATACAAGA | 20 | −31.0 | 49.4–58.0 | 49.4 | +0.5 | −5.3 |
| [22] | ATTATTGAAG | | | | | | |
| H | TTCTCTGTAA | 20 | −31.5 | 51.9–60.0 | 51.9 | −0.8 | −5.3 |
| [23] | AGAACATG AA | | | | | | |
| I | TGTAATATAG | 22 | −33.5 | 50.9–60.1 | 50.9 | +1.5 | −5.3 |
| [24] | ATGAGGTAAT TT | | | | | | |

Each ligation reaction mixture had a volume of 10 ul, and was made by mixing together the following stocks: 5 ul of a oligonucleotide solution 500 femtomoles each of oligos B and C and 250 femtomoles of each of oligos D–I to the reaction mixture; 2 ul of beads attached to the biotinylated PCR product and suspended in water; and 3 ul of ligase component. The oligo mix and beads were added on ice and layered with 7 ul of oil. The mixture was denatured for two minutes at 94° C. on a Robocycler prior to the addition of the ligase mixture.

Each 3 ul of ligase component contained 1 ul ligase buffer (10× Pfu Ligase Buffer (Stratagene)); 0.5 ul ligase enzyme (4 U/ul, Pfu DNA Ligase (Stratagene)); 0.5 ul water, and 0.1 ul oligo A solution containing 1 pmol/ul, thus giving 1 pmol of A per reaction. Oligo A was labeled with Cy 5.5 for detection.

The ligation reaction was run on the Robocyler using the following program:
2 minutes initial denaturation −94° C.
then 8–9 cycles of
    30 seconds 94° C.
    15 minutes 58° C.
The reaction was diluted with 10 ul of stop buffer and run on an electrophoresis gel for evaluation of the ligation products.

The results observed for several samples analyzed on a MicroGene Blaster™ DNA sequencing apparatus (Visible Genetics Inc) are shown in FIGS. 15A–D. FIG. 15 A shows the fragment pattern detected when a wild type gene exactly matching the sequence of the oligos is evaluated. The A peak reflects excess unreacted oligo A. The B–I peaks represent ligation products extending from oligo to the indicated oligo. Thus, in FIG. A, there was a substantial amount of ligation product ending after the E or F oligos and the full length product ending with the I oligo.

Figure 15A:
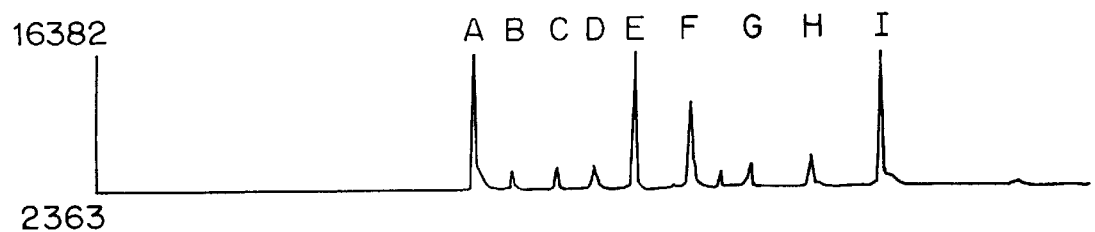
Figure 15B:
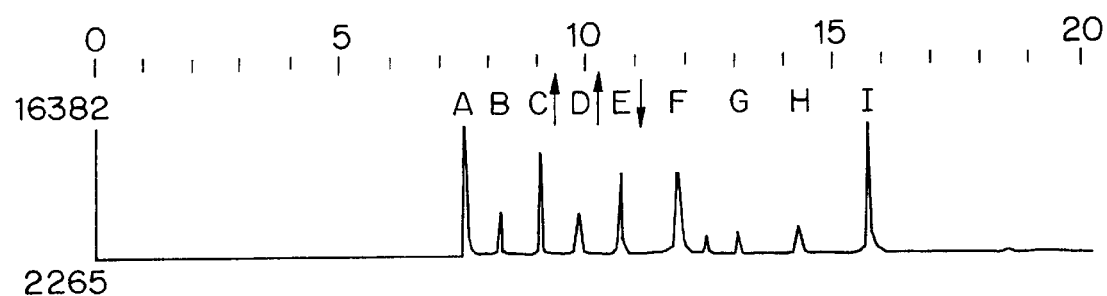

FIG. 15B shows the results for a heterozygous C→T mutation near the end of the D oligo. This results in an increase in the amount of product ending with the B, C or D fragment, and a decrease in the amount of product ending with the E fragments, but little or no change in the amount of product ending in the F fragment.

Figure 15C:
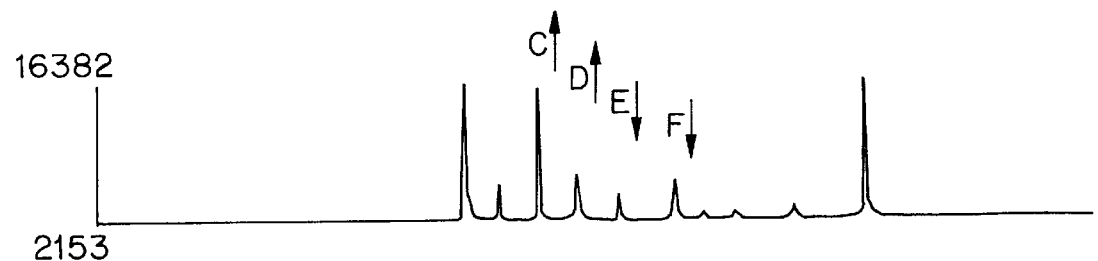

FIG. 15C shows the results for a homozygous base change near the end of the D oligo. In this case, the products ending with the B, C and D fragments increase, while the products ending with the E and F fragments decrease.

Figure 15D:
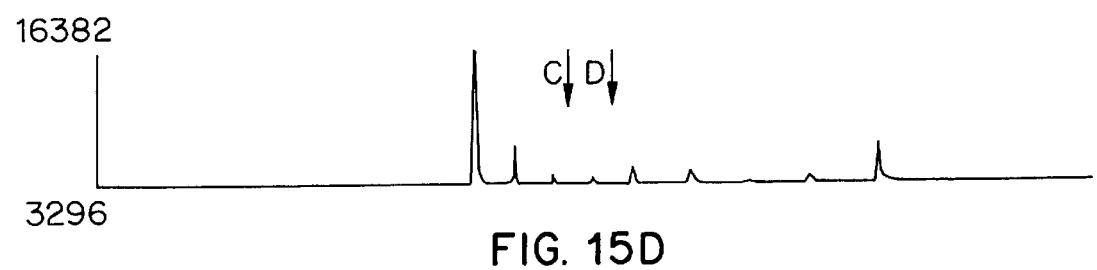

FIG. 15D shows the results for a heterozygous mutant in the C oligo. An increase in the products ending in the B oligo is seen, while the amounts of all other products decreases.

While the foregoing discussion and examples exemplify the invention in terms of detection of point mutations, the method of the invention is equally applicable to detection of mutations of other types. Quite clearly, even small deletions or insertions will lead to a greater disruption of the hybridization of the probe which overlaps the mutation and thus they will be easily detectable using the method of the invention. Several other issues bear mention however.

One such issue is the ability of the assay of the invention to detect certain mutations which lead to a G:T wobble pair being formed between the probe and the mutant target. The properties of a G:T wobble-pair within an oligonucleotide duplex have been carefully examined by NMR and calorimetry (Patel et al., 1982b; Hare et al., 1986; Kalnik et al., 1988). Two basic properties of the perfectly-matched duplex are preserved in the duplex that contains the G:T wobble-pair. (i) There is hydrogen-bonding between the two nucleotide bases of the wobble-pair. (ii) There is a stacking interaction between the wobble-pair and each adjacent base-pair.

Although these basic properties of a normal base-pair are preserved, nonetheless a G:T wobble-pair will significantly destabilize a short DNA duplex (Patel et al., 1982b). This decrease in stability is caused by two local properties of the wobble-pair: (i) a weaker stacking with adjacent base-pairs (Patel et al., 1982b; Kneale et al., 1985) and (ii) altered conformations at the phosphodiester linkages which connect the wobble-pair to the adjacent base-pairs (Patel et al., 1982b). The destabilizing influence of a wobble-pair is revealed at the kinetic level by an enhanced tendency of a wobble-pair containing terminus of an oligonucleotide duplex to "fray" at temperatures significantly below Tm (Patel et al., 1982b). Based on these physical studies, it is expected that G:T wobble pairs will destabilize a probe-target duplex sufficiently so that mutations of this type will be detectable. It is also possible to implement the assay in a format where the two strands of the gene are used individually, each with its own set of probes. A G:T wobble pair in one assay would have a corresponding C:A mispair in the other assay which would be easily detectable.

Figure 14:
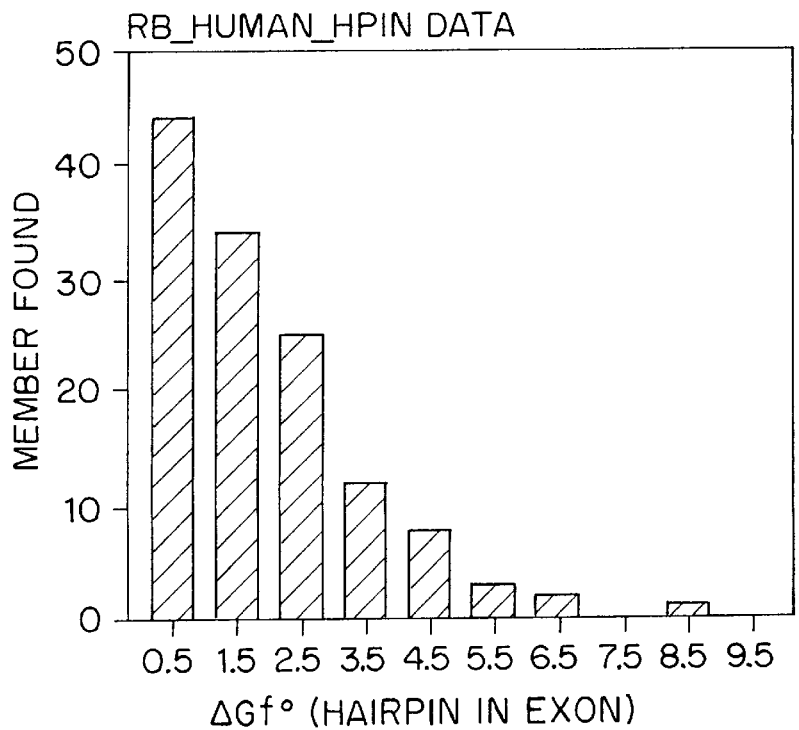
FIG. 14 shows statistical plot of the distribution of stabilities of duplex structures in the human retinoblastoma coding sequence.

Unwanted secondary structure may also introduce challenges to performing the assay of the invention. If the single-stranded form of an exon happens to possess a large amount of internal secondary structure, this could interfere with hybridization of the oligonucleotide probes. Similarly, if one of the probes has excessive secondary structure, its hybridization with the target DNA strand (T) may be impaired. To assess the prevalence and importance of secondary structure elements in a typical gene, we have used the "Oligo" program to examine six of the 27 exons of the human retinoblastoma gene (exons 1, 8, 17, 19, 20 and 23) for stem-loop structures. All structures with $\Delta G_f°<0$ kcal/mol were considered. A statistical plot of the distribution of stabilities is shown in FIG. 14. This distribution has a negative-exponential form, which emphasizes the rarity of highly stable secondary structure elements in exons which most likely have been selected against during evolution.

When a gene is examined as a candidate for the assay of the invention, such a stability plot can be easily made. In addition, both strands of an exon will be examined, and the one with the least internal secondary structure, and least tendency to form self-duplexes, will be designated the target strand (T). This evaluation might be performed on an exon-by-exon basis, between coding and non-coding strands, to choose the best strand to designate as "target" (T) in the assay. Denaturants might also be used if needed, although it should be noted that under typical assay conditions (i.e., ~65° C.), most secondary structure elements will be melted out.

A further issue is the possibility of template-independent ligation occurring in the solution. Non-thermostable DNA ligases from *E. coli* and phage T4 have been shown, under certain conditions, to catalyze the ligation of single-stranded oligonucleotides in the absence of a complementary DNA template (Barringer et al., 1990; Edwards et al., 1991). If such an activity were present in the assay of the invention, it might cause the oligonucleotide which spans the site of a mutation to be ligated to other oligonucleotides that are present in the assay. Such a false ligation event would therefore produce the "false negative" inference that a mutation does not exist in the target (T), when in fact the mutation really does exist.

Non-templated ligation also occurs with thermostable DNA ligases (Abravaya et al., 1995). There are significant differences in this tendency, however, between different types of thermostable ligase. Marsh et al. (1992) compared this aberrant activity for DNA ligases from Pyrococcus furiosus and Thermus thermophilus. They found that the P. furiosus enzyme had the least non-templated ligase activity, and it is therefore a preferred enzyme for use in the present invention. As noted above, however, other enzymes can be used provided that the conditions are selected to minimize template-independent ligation.

Notwithstanding the general applicability of the assay method of the invention, there is at least one very rare form of mutation, a G:A tandem mispair, which may be difficult or impossible to detect using the method of this invention. It has been found that G:A tandem-mispairs can greatly stabilize a nucleic acid duplex (Lin et al., 1991a, 1991b; Ebel et al., 1992). These mispairs have the following form:

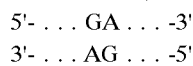

There is even a case where a 10-mer duplex with multiple G:A tandem-mispairs is more stable than the wild-type homologue with no mispairs (Li et al., 1991b; Lane et al., 1994). The mutant duplexes appear to gain their extra stability by unusual hydrogen-bonding, purine-purine stacking, and favorable base-dipole orientations at the sites of the tandem-mispairs, even though they retain the canonical B-form overall (Li et al., 1991b). The sequence which immediately flanks the tandem-mismatch has a modifying effect on stability (Ebel et al., 1992). No anomalous stability is observed for sequences that contain single GA or AG mispairs, or that contain tandem mispairs in the reverse orientation (5'-AG-3' instead of 5'-GA'3') (Lin et al., 1991b).

Because of the anomalous stability of tandem G:A mispair, such mutation will be very difficult, if not impossible, to detect by the method of the invention. This particular type of mismatch should be quite rare, however, as it requires two independent & adjacent point mutations, and thus does not significantly detract from the general applicability of the invention.

We claim:

1. A method for detection of mutations within a target gene or gene fragment in a sample, said target gene or gene fragment having a known wild-type sequence, comprising the steps of:
   (a) combining the sample with at least three species of oligonucleotide probes, a labeled 3'-probe, a labeled 5'-probe and at least one intermediate probe, under hybridization conditions, said species of oligonucleotide probes having sequences which are perfectly complementary to and hybridize with sequential and contiguous portions of the wild-type sequence, to preferentially form duplex structures between the target gene or gene fragment and those species of oligonucleotide probes which are perfectly complementary to the target gene or gene fragment, said at least three oligonucleotide probes including probes which are different in sequence from one another;
   (b) ligating the hybridized oligonucleotide probes to join those oligonucleotide probes which hybridize to the gene fragment in ligatable proximity to one another to form one or more species of ligation products; and
   (c) evaluating the species of ligation products by separating the ligation products into subgroups based upon the size of the ligation product and detecting the labels associated with the labeled 3'-probe and the labeled 5'-probe, wherein the ligation reaction is conducted under conditions such that variations between the wild-type sequence and the target sequence which are intermediate in location between the 5' and 3'-end bases of the probes result in a different product mixture than those obtained in the absence of such variations, and wherein a difference in length or quantity between the ligation products formed and standard values obtained using a wild-type target is indicative of the presence of a mutation in the gene or gene fragment in the sample.

2. A method according to claim 1, wherein the labels are fluorescent.

3. A method according to claim 2, wherein the label is fluorescein.

4. A method according to claim 1, wherein the sample is combined with from 3 to 10 species of probes.

5. A method according to claim 1, wherein the sample is combined with from 5 to 10 species of probes.

6. A method according to claim 1, wherein each probe contains from 15 to 25 bases.

7. A method according to claim 1, wherein the species of oligonucleotide probes all have a calculated melting temperature within a range of 10 degrees C. of each other.

8. A method according to claim 1, further comprising the step of amplifying the target gene or gene fragment prior to hybridizing it with the oligonucleotide probes.

9. A method according to claim 8, wherein the target gene or gene fragment is amplified by PCR amplification.

10. A method according to claim 1, wherein the species of oligonucleotide probe are combined with the sample at a concentration of from 5 to 40 nM of each probe.

11. A method according to claim 1, wherein the detectable labels are fluorescent.

12. A method according to claim 11, wherein the detectable labels are different from one another.

13. A method according to claim 1, wherein the target gene or gene fragment is labeled with a detectable label.

14. A method according to claim 1, wherein the ligation products are separated by gel electrophoresis.

15. A method according to claim 14, wherein the separated subgroups are detected in real time during migration through an electrophoresis gel.

16. A method according to claim 14, wherein the subgroups are detected using a fluorescence detector.

17. A kit for detection of the presence of mutations within a gene or gene fragment having a known wild-type sequence comprising at least five species of oligonucleotide probes, said probes having sequences which are perfectly complementary to and hybridize with sequential and contiguous portions of one strand of the wild-type sequence and having terminal groups such that the probes are enzymatically ligatable one to the other when hybridized to the wild-type sequence, and said at least five species including probes having sequences which are different from one another.

18. A kit according to claim 17, wherein at least one of the species of probes is labeled with a detectable label.

19. A kit according to claim 18, wherein the detectable label is a fluorescent label.

20. A kit according to claim 17, further comprising, in packaged combination with the oligonucleotide probes, a ligase enzyme.

21. A kit according to claim 17, further comprising, in packaged combination with the oligonucleotide probes, a pair of amplification primers for amplifying the gene or gene fragment.

22. A kit according to claim 21, wherein one of the pair of amplification primers is labeled with a fluorescent label.

23. A kit according to claim 21, wherein one of the pair of amplification primers is biotinylated.

24. A kit according to claim 17, wherein at least two of the species of probes is labeled with a detectable label.

25. A kit according to claim 23, wherein one of the labeled oligonucleotide probes hybridizes to and is complementary with the portion of the wild-type sequence which is closest to the 3'-end of the gene or gene fragment, and the other of the labeled oligonucleotide probes hybridizes to and is complementary with the portion of the wild-type sequence which is closest to the 5'-end of the gene or gene fragment.

26. A composition for detection of mutations within a gene or gene fragment having a known wild-type sequence, comprising a mixture of at least five species of oligonucleotide probes, said probes having sequences which are perfectly complementary to and hybridize with sequential and contiguous portions of one strand of the wild-type sequence and having terminal groups such that the probes are enzymatically ligatable one to the other when hybridized to the wild-type sequence, and said at least five species including probes having sequences which are different from one another.

27. The composition according to claim 26, wherein at least one of the oligonucleotide probes is labeled with a detectable label.

28. The composition according to claim 27, wherein the detectable label is a fluorescent label.

* * * * *

UNITED STATES PATENT AND TRADEMARK OFFICE
CERTIFICATE OF CORRECTION

| | | |
|---|---|---|
| PATENT NO. | : 6,025,139 | Page 1 of 1 |
| APPLICATION NO. | : 09/011821 | |
| DATED | : February 15, 2000 | |
| INVENTOR(S) | : James M. Dunn and Thomas D. Yager | |

It is certified that error appears in the above-identified patent and that said Letters Patent is hereby corrected as shown below:

On the Title page,

Item [74], "Oppendahl" should read -- Oppedahl --

Signed and Sealed this

Eighteenth Day of May, 2010

David J. Kappos
*Director of the United States Patent and Trademark Office*

```
                         SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 61
         (B) TYPE: nucleic acid
         (C) STRANDEDNESS: double
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: internal segment of human k-ras gene (xi) SEQUENCE DESCRIPTION: SEQ ID NO:1:

TATCGTCAAG GCACTCTTGC CTACGCCACC AGCTCCAACT                        40

ACCACAAGTT TATATTCAGT C                                           61

(2) INFORMATION FOR SEQ ID NO:2:

(i) SEQUENCE CHARACTERISTICS:
         (A) LENGTH: 23
         (B) TYPE: nucleic acid
         (C) STRANDEDNESS: double
         (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
         (A) ORGANISM: human (ix) FEATURE:
         (A) NAME/KEY: probe of portion of human k-ras gene (xi) SEQUENCE DESCRIPTION: SEQ ID NO:2:

GACTGAATAT AAACTTGTGG TAG                                         23

(2) INFORMATION FOR SEQ ID NO:3:

(i) SEQUENCE CHARACTERISTICS:
         (A) LENGTH: 18
         (B) TYPE: nucleic acid
         (C) STRANDEDNESS: double
         (D) TOPOLOGY: linear
```

(ii) MOLECULE TYPE: other DNA (iii) HYPOTHETICAL: no (iv) ANTI-SENSE: yes (v) FRAGMENT TYPE: internal (vi) ORIGINAL SOURCE:
             (A) ORGANISM: human (ix) FEATURE:
             (A) NAME/KEY: probe of portion of human k-ras gene (xi) SEQUENCE DESCRIPTION: SEQ ID NO:3:

TTGGAGCTGG TGGCGTAG                                                       18

(2) INFORMATION FOR SEQ ID NO:4:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
             (A) ORGANISM: human (ix) FEATURE:
             (A) NAME/KEY: probe of portion of human k-ras gene (xi) SEQUENCE DESCRIPTION: SEQ ID NO:4:

GCAAGAGTGC CTTGACGATA                                                     20

(2) INFORMATION FOR SEQ ID NO:5:

(i) SEQUENCE CHARACTERISTICS:
             (A) LENGTH: 18
             (B) TYPE: nucleic acid
             (C) STRANDEDNESS: double
             (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
             (A) ORGANISM: human (ix) FEATURE:
             (A) NAME/KEY: probe of portion of human k-ras gene with one
                 mismatch (xi) SEQUENCE DESCRIPTION: SEQ ID NO:5:

TTGGAGCTGG TGGCGTAC                                                       18

(2) INFORMATION FOR SEQ ID NO:6:

(i) SEQUENCE CHARACTERISTICS:
             (A) LENGTH: 18
             (B) TYPE: nucleic acid

```
        (C) STRANDEDNESS: double
        (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: probe of portion of human k-ras gene with one
            mismatch (xi) SEQUENCE DESCRIPTION: SEQ ID NO:6:

TTGGAGCTGG TGGCCTAG                                                18

(2) INFORMATION FOR SEQ ID NO:7:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: probe of portion of human k-ras gene with one
            mismatch (xi) SEQUENCE DESCRIPTION: SEQ ID NO:7:

TTGGAGCTGG TCGCGTAG                                                18

(2) INFORMATION FOR SEQ ID NO:8:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: probe of portion of human k-ras gene with one
            mismatch (xi) SEQUENCE DESCRIPTION: SEQ ID NO:8:

TTGGAGCTCG TGGCGTAG                                                18
```

(2) INFORMATION FOR SEQ ID NO:9:

(i) SEQUENCE CHARACTERISTICS:
        (A) LENGTH: 111
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: internal portion of human k-ras gene, exon 1

(xi) SEQUENCE DESCRIPTION: SEQ ID NO:9:

```
ATGACTGAAT ATAAACTTGT GGTAGTTGGA GCTGGTGGCG                    40

TAGGCAAGAG TGCCTTGACG ATACAGCTAA TTCAGAATCA                    80

TTTTGTGGAC GAATATGATC  CAACAATAGA G                           111
```

(2) INFORMATION FOR SEQ ID NO:10:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: amplification primer for portion of human k-ras
            gene (xi) SEQUENCE DESCRIPTION: SEQ ID NO:10:

```
GGCCTGCTGA AAATGACTGA                                          20
```

(2) INFORMATION FOR SEQ ID NO:11:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:

(A) NAME/KEY: amplification primer for portion of human k-ras
            gene (xi) SEQUENCE DESCRIPTION: SEQ ID NO:11:

GTCCTGCACC AGTAATATGC                                                    20

(2) INFORMATION FOR SEQ ID NO:12:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (A) NAME/KEY: amplification primer for portion of human k-ras
            gene (xi) SEQUENCE DESCRIPTION: SEQ ID NO:12:

GACTGAATAT AAACTTGTGG                                                    20

(2) INFORMATION FOR SEQ ID NO:13:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: amplification primer for portion of human k-ras
            gene (xi) SEQUENCE DESCRIPTION: SEQ ID NO:13:

TATTGTTGGA TCATATTCG                                                     19

(2) INFORMATION FOR SEQ ID NO:14:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (A) NAME/KEY: probe for portion of human k-ras gene (xi) SEQUENCE DESCRIPTION: SEQ ID NO:14:

CAGCTAATTC AGAATCATTT TGT                                                23

(2) INFORMATION FOR SEQ ID NO:15:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: other DNA (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (A) NAME/KEY: probe for portion of human k-ras gene (xi) SEQUENCE DESCRIPTION: SEQ ID NO:15:

GGACGAATAT GATCCAACAA TA                                                 22

(2) INFORMATION FOR SEQ ID NO:16:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: probe for exon 8 of RB1

(xi) SEQUENCE DESCRIPTION: SEQ ID NO:16:

TTTACCACTT TTACAGAAAC                                                    20

(2) INFORMATION FOR SEQ ID NO:17:

(i) SEQUENCE CHARACTERISTICS:
            (A) LENGTH: 19
            (B) TYPE: nucleic acid
            (C) STRANDEDNESS: double
            (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
                (A) ORGANISM: human (ix) FEATURE:
                (A) NAME/KEY: probe for exon 8 of RB1

(xi) SEQUENCE DESCRIPTION: SEQ ID NO:17:

AGCTGTTATA CCCATTAAT                                                19

(2) INFORMATION FOR SEQ ID NO:18:

(i) SEQUENCE CHARACTERISTICS:
                (A) LENGTH: 16
                (B) TYPE: nucleic acid
                (C) STRANDEDNESS: double
                (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
                (A) ORGANISM: human (ix) FEATURE:
                (A) NAME/KEY: probe for exon 8 of RB1

(xi) SEQUENCE DESCRIPTION: SEQ ID NO:18:

GGTTCACCTC GAACAC                                                   16

(2) INFORMATION FOR SEQ ID NO:19:

(i) SEQUENCE CHARACTERISTICS:
                (A) LENGTH: 14
                (B) TYPE: nucleic acid
                (C) STRANDEDNESS: double
                (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
                (A) ORGANISM: human (ix) FEATURE:
                (A) NAME/KEY: probe for exon 8 of RB1

(xi) SEQUENCE DESCRIPTION: SEQ ID NO:19:

CCAGGCGAGG TCAG                                                     14

(2) INFORMATION FOR SEQ ID NO:20:

(i) SEQUENCE CHARACTERISTICS:
                (A) LENGTH: 15
                (B) TYPE: nucleic acid
                (C) STRANDEDNESS: double
                (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: probe for exon 8 of RB1

(xi) SEQUENCE DESCRIPTION: SEQ ID NO:20:

AACAGGAGTG CACGG                                                            15

(2) INFORMATION FOR SEQ ID NO:21:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: probe for exon 8 of RB1

(xi) SEQUENCE DESCRIPTION: SEQ ID NO:21:

ATAGCAAAAC AACTAGAAAA                                                       20

(2) INFORMATION FOR SEQ ID NO:22:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: probe for exon 8 of RB1

(xi) SEQUENCE DESCRIPTION: SEQ ID NO:22:

TGATACAAGA ATTATTGAAG                                                       20

(2) INFORMATION FOR SEQ ID NO:23:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other DNA

```
        (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: probe for exon 8 of RB1

(xi) SEQUENCE DESCRIPTION: SEQ ID NO:23:

TTCTCTGTAA AGAACATGAA                                                          20

(2) INFORMATION FOR SEQ ID NO:24:

(i) SEQUENCE CHARACTERISTICS:
             (A) LENGTH: 22
             (B) TYPE: nucleic acid
             (C) STRANDEDNESS: double
             (D) TOPOLOGY: linear (ii) MOLECULE TYPE: other DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: probe for exon 8 of RB1

(xi) SEQUENCE DESCRIPTION: SEQ ID NO:24:

TGTAATATAG ATGAGGTAAT TT                                                       22
```